(12) United States Patent
Frances

(10) Patent No.: US 7,893,130 B2
(45) Date of Patent: *Feb. 22, 2011

(54) PHOTOCURABLE DENTAL COMPOSITION

(75) Inventor: Jean-Marc Frances, Meyzieu (FR)

(73) Assignee: Bluestar Silicones France SAS, Lyons (FR)

( * ) Notice: Subject to any disclaimer, the term of this patent is extended or adjusted under 35 U.S.C. 154(b) by 449 days.

This patent is subject to a terminal disclaimer.

(21) Appl. No.: 11/125,133

(22) Filed: May 10, 2005

(65) Prior Publication Data

US 2005/0277705 A1 Dec. 15, 2005

Related U.S. Application Data

(60) Provisional application No. 60/599,021, filed on Aug. 6, 2004.

(30) Foreign Application Priority Data

May 13, 2004 (FR) .................. 04 05176
Jun. 30, 2004 (FR) .................. 04 07210

(51) Int. Cl.
| | |
|---|---|
| A61K 6/087 | (2006.01) |
| A61C 5/00 | (2006.01) |
| C07D 335/16 | (2006.01) |
| C07D 303/02 | (2006.01) |
| G03F 7/029 | (2006.01) |
| C08F 2/50 | (2006.01) |
| C08G 59/20 | (2006.01) |
| C08G 59/68 | (2006.01) |
| A61L 27/34 | (2006.01) |

(52) U.S. Cl. ................ 523/115; 522/25; 522/26; 522/27; 522/53; 522/31; 522/49; 522/170; 522/908; 549/27; 433/228.1; 106/35

(58) Field of Classification Search .......... 523/115, 523/116, 118; 522/148, 25, 26, 27, 31, 49, 522/53, 170, 908; 433/228.1; 106/35; 549/27
See application file for complete search history.

(56) References Cited

U.S. PATENT DOCUMENTS

| | | | | | |
|---|---|---|---|---|---|
| 4,791,213 | A | * | 12/1988 | Gawne et al. | 549/27 |
| 5,693,688 | A | * | 12/1997 | Priou | 522/25 |
| 6,011,180 | A | * | 1/2000 | Cunningham et al. | 568/6 |
| 6,025,017 | A | * | 2/2000 | Roth | 427/146 |
| 6,045,974 | A | * | 4/2000 | Cunningham et al. | 430/281.1 |
| 6,245,828 | B1 | * | 6/2001 | Weinmann et al. | 522/148 |
| 6,747,071 | B1 | * | 6/2004 | Frances | 522/148 |
| 7,740,482 | B2 | * | 6/2010 | Frances et al. | 433/215 |
| 2003/0035899 | A1 | * | 2/2003 | Klettke et al. | 427/387 |
| 2003/0211338 | A1 | * | 11/2003 | Frances et al. | 428/447 |
| 2004/0006154 | A1 | * | 1/2004 | Ibaragi et al. | 523/115 |

FOREIGN PATENT DOCUMENTS

| | | | | |
|---|---|---|---|---|
| JP | 2001206903 | A | * | 7/2001 |
| WO | WO0019967 | A1 | * | 4/2000 |

* cited by examiner

*Primary Examiner*—Mark Eashoo
*Assistant Examiner*—Michael Pepitone
(74) *Attorney, Agent, or Firm*—Buchanan, Ingersoll & Rooney, P.C.

(57) ABSTRACT

Dental compositions are described which are photocurable by radiation with a wavelength greater than 390 nm. The compositions include a cationically active compound, a dental filler, optionally a dispersant, a cationic photoinitiator and a photosensitizer which is a thioxanthone salt substituted by at least one group containing an ammonium function. The composition has the advantage of remedying the color stability problems of finished dental products after crosslinking.

19 Claims, No Drawings

PHOTOCURABLE DENTAL COMPOSITION

CROSS-REFERENCE TO PRIORITY/PCT/PROVISIONAL APPLICATIONS

This application claims priority under 35 U.S.C. §119 of French Application No. 04 05176, filed May 13, 2004, and French Application No. 04 07210, filed Jun. 30, 2004, and of U.S. provisional application No. 60/599,021, filed Aug. 6, 2004, each expressly incorporated by reference and each assigned to the assignee hereof.

BACKGROUND

1. Field of the Invention

The field of the invention is that of dental compositions. More specifically the dental compositions developed in the context of the present invention can be used for producing dental prostheses and for dental restoration.

2. Related Art

These dental compositions are conventionally epoxy resins, or photocurable silicones or free-radically polymerizable acrylate resins. These compositions further include particulate reinforcing fillers (of hydrophobicized silica, for example), photoinitiators, and, optionally, photosensitizers, and even other functional additives such as pigments or stabilizers.

After they have been mixed, these compositions are shaped and then photocrosslinked to a structural mass similar to that of the teeth.

For example, patent application FR-A-2 784 025 describes dental compositions based on silicone resins which are polymerizable/crosslinkable cationically and under irradiation, with or without subsequent thermal postcrosslinking. These silicone resins contain oxirane (epoxide, oxetane, etc.) or vinyl ether functionalities. Such compositions comprise:

one or more cationically polymerizable and/or crosslinkable polydimethylsiloxanes which carry at one at least of their ends reactive functions of formula:

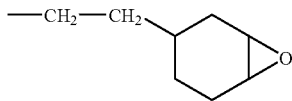

an effective amount of at least one onium borate initiator:

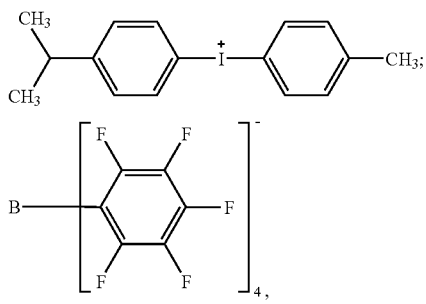

at least one photosensitizer, and
at least one inert dental or reinforcing filler based on dental glasses, polymethyl methacrylate or pyrogenic silica, optionally treated with hexamethyldisilazane or polydimethylsiloxane, with a specific surface area of 200 m²/g.

These dental compositions are intended for the manufacture of dental prostheses or dentures and for dental restoration.

These silicones have the advantage over cationically crosslinking organic resins of being highly transparent to UV-visible light and therefore of enabling the production of very thick materials (several millimeters thick) which are photocrosslinked within a very short time (less than a minute) with a UV lamp emitting in the visible range >400 nm.

These silicones, however, are formulated with iodonium salts and photosensitizers, especially thioxanthones, which give rise to great color variation when exposed to radiation with a wavelength greater than 390 nm during photocrosslinking. This is manifested in a pinkish coloration in the end product (after exposure), which is undesirable from an esthetic standpoint. Moreover, another problem resulting from the use of photosensitizers concerns inadequate crosslinking kinetics when very thick materials (several millimeters thick) are prepared.

It is therefore apparent that the prior art does not provide a satisfactory solution to the twin problem of the low color stability of finished dental products (after crosslinking) and of the inadequate crosslinking kinetics when very thick materials (several millimeters thick) are prepared.

SUMMARY OF THE INVENTION

One of the essential objectives of the present invention is therefore to remedy this by providing new photocurable dental compositions, based in particular on units which are cationically polymerizable under UV (oxiranes, for example), which do not exhibit the drawbacks of the prior art.

These objectives, among others, are attained by the present invention, which first provides a dental composition photocurable by radiation with a wavelength greater than 390 nm, comprising:

(1) at least one cationically reactive compound (A);
(2) at least one dental filler (B);
(3) optionally at least one dispersant (C) comprising at least one organic polymer or copolymer;
(3) at least one cationic photoinitiator (D); and
(4) at least one photosensitizer (E) which is a thioxanthone salt substituted by at least one group G containing an ammonium function, the said photosensitizer (E), optionally in combination with at least one camphorquinone, phenanthrenequinone and/or substituted anthracene, has the formula:

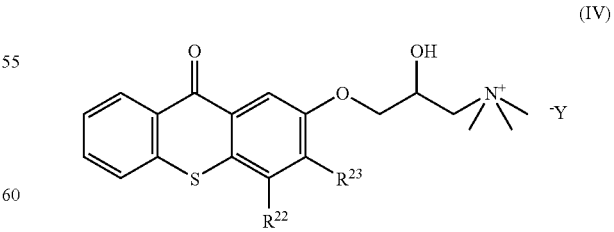

(IV)

in which:

$R^{22}$ and $R^{23}$ are identical or different and represent a hydrogen or an optionally substituted C1-C10 alkyl radical; preferably $R^{22} = R^{23} =$ methyl, (Y⁻) being an anionic entity selected from the group consisting of: $BF_4^-$, $PF_6^-$; $SbF_6^-$; the anion (I) of formula $[BX_aR_b]^-$ defined below, $R_fSO_3^-$; $(R_fSO_2)_3C^-$ or $(R_fSO_2)_2N^-$, where $R_f$ is a linear or branched alkyl radical substituted by at least one halogen atom, preferably a fluorine atom, and even more preferably (Y⁻) is selected from the borates of the following formulae: $[B(C_6H_3(CF_3)_2)_4]^-$ and $[B(C_6F_5)_4]^-$;

the said anion (I) of formula $[BX_aR_b]^-$ being defined in the following manner:

a and b are integers ranging from 0 to 3 for a and from 1 to 4 for b, with a+b=4, the symbols X represent:
  a halogen (chlorine, fluorine) atom, with a=0 to 3, or
  an OH function, with a=0 to 2, the symbols R are identical or different and represent:
  a phenyl radical substituted by at least one electron-withdrawing group such as, for example, $OCF_3$, $CF_3$, $NO_2$ or CN and/or by at least two halogen atoms (especially fluorine), when the cationic entity is an onium of an element from groups 15 to 17,
  a phenyl radical substituted by at least one electron-withdrawing element or group, in particular a halogen atom (especially fluorine), $CF_3$, $OCF_3$, $NO_2$ or CN, when the cationic entity is an organometallic complex of an element from groups 4 to 10, or
  an aryl radical containing at least two aromatic nuclei, such as, for example, biphenyl, naphthyl, optionally substituted by at least one electron-withdrawing element or group, in particular a halogen atom, especially fluorine, $OCF_3$, $CF_3$, $NO_2$ or CN, irrespective of the cationic entity.

It is to the inventors' merit to have shown, surprisingly and unexpectedly, that a certain class of thioxanthone makes it possible to remedy the problems associated with the use of photosensitizers, namely the low color stability of the finished dental products (after crosslinking) and the inadequate crosslinking kinetics when very thick dental materials (several millimeters thick) are prepared.

DESCRIPTION OF PREFERRED EMBODIMENTS

According to one very advantageous embodiment, the photosensitizer (E) and the cationic photoinitiator (D) are selected such that they are composed of the same anion; the anion preferably is selected from the borates of the following formulae: $[B(C_6H_3(CF_3)_2)_4]^-$ and $[B(C_6F_5)_4]^-$.

As a particularly preferred embodiment the photosensitizer (E), optionally in combination with at least one camphorquinone, phenanthrenequinone and/or substituted anthracene, is selected from the compounds of the formula:

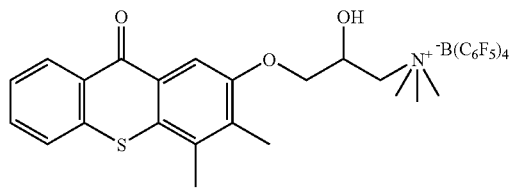

(V)

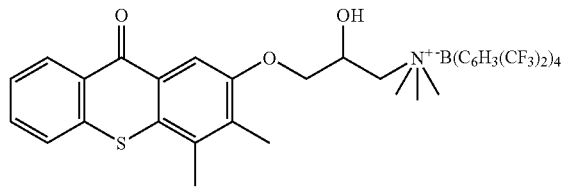

(VI)

The cationically reactive compounds (A) useful according to the invention may include the monomers and/or (co)polymers comprising:

epoxides, vinyl ethers, oxetanes, spiro-ortho-carbonates, spiro-ortho-esters and combinations thereof.

According to one preferred embodiment the cationically reactive compound (A) is composed of at least one silicone oligomer or polymer (A-1) which is crosslinkable and/or polymerizable, is liquid at ambient temperature or thermofusible at a temperature lower than 100° C., and comprises:
a) at least one unit of the following formula:

(M-1)

in which:
  a=0, 1 or 2,
  R⁰, identical or different at each occurrence, represents an alkyl, cycloalkyl, aryl, vinyl, hydrogeno or alkoxy radical, preferably a C1-C6 lower alkyl,
  Z, identical or different at each occurrence, is an organic substituent containing at least one reactive oxirane, alkenyl ether, oxetane, dioxolane and/or carbonate function, and
b) at least two silicon atoms.

The unit (M-1) preferably comprises substituents Z selected from the group consisting of the following radicals:

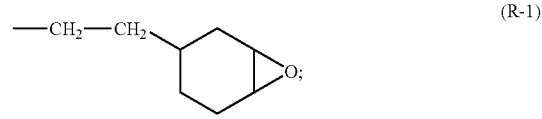

(R-1)

(R-2)

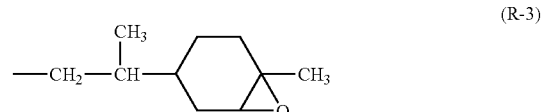

(R-3)

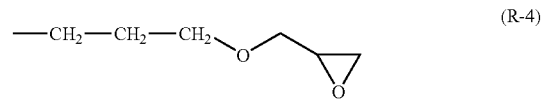

(R-4)

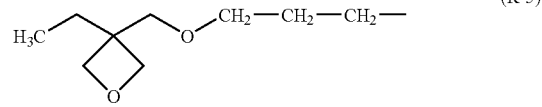

(R-5)

-continued

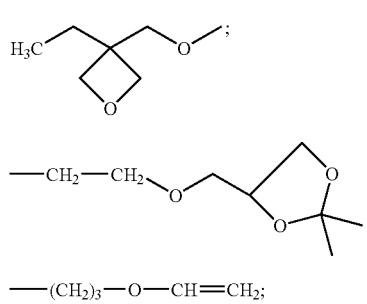  (R-6)

(R-7)

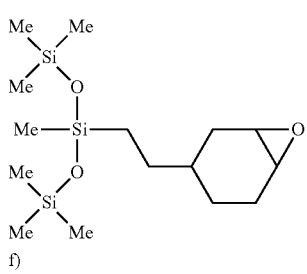

—(CH$_2$)$_3$—O—CH=CH$_2$;  (R-8)

-continued

—(CH$_2$)$_3$—O—CH=CH—R″  (R-9)

with R″ representing a C$_1$-C$_6$ linear or branched alkyl radical.

According to a second advantageous version of the present invention, the silicone oligomer or polymer (A-1) is composed of at least one silicone whose average formula corresponds to one of the formulae selected from the group consisting of the formulae (S-1) to (S-92) described below:

a)

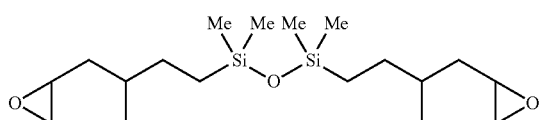  (S-1)

b)

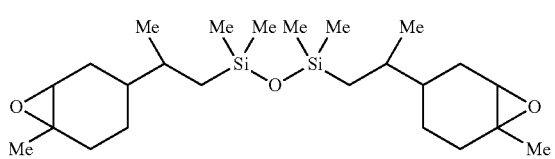  (S-2)

c)

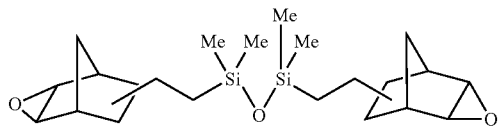  (S-3)

d)

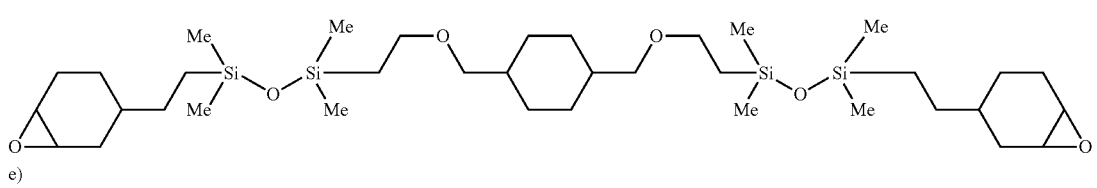  (S-4)

e)

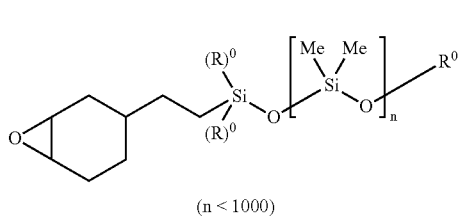  (S-5)

f)

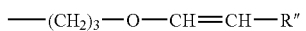  (S-6)

(n < 1000)

-continued
g)
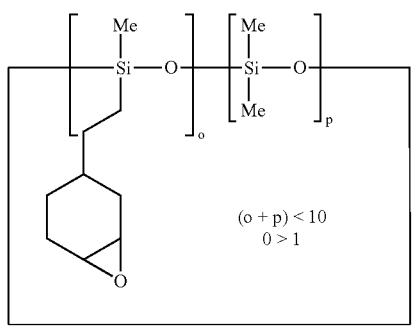
(S-7)
h)
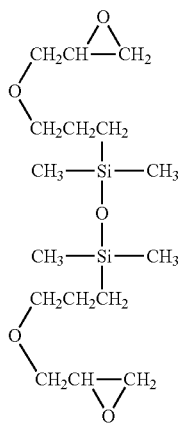
(S-8)
i)
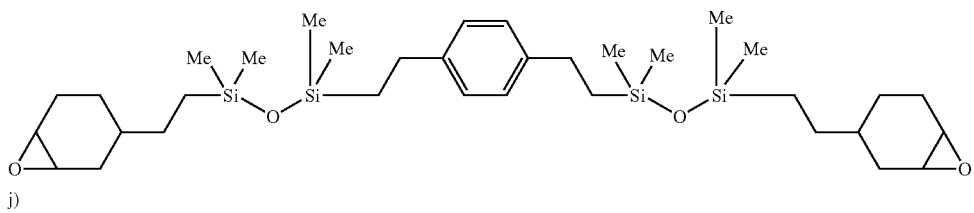
(S-9)
j)
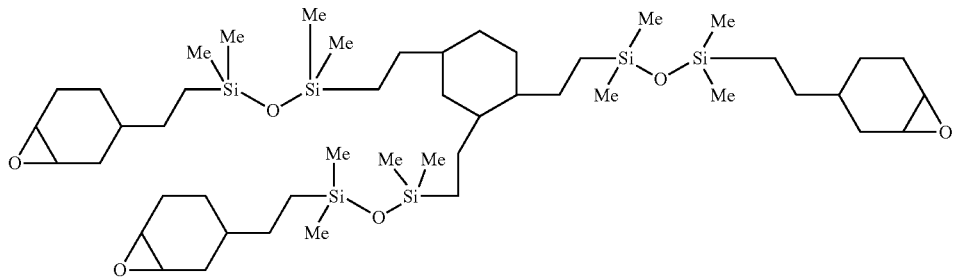
(S-10)
k)
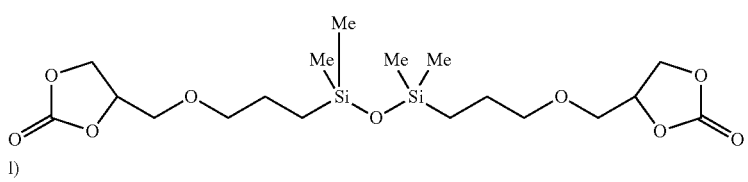
(S-11)
l)

-continued
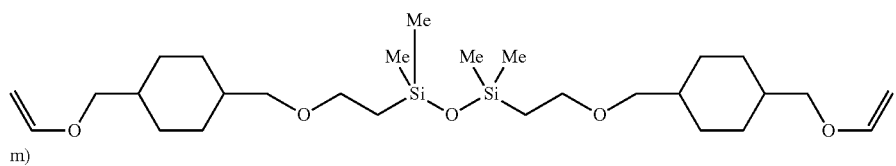
(S-12)
m)
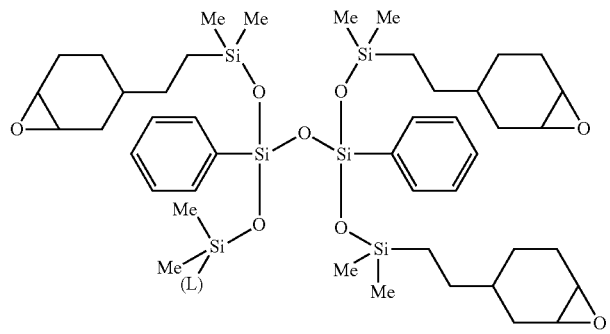
(S-13)
where L=H; OH; Me; phenyl; C1-C12 alkyl; C1-C6 cycloalkyl; or the groups:
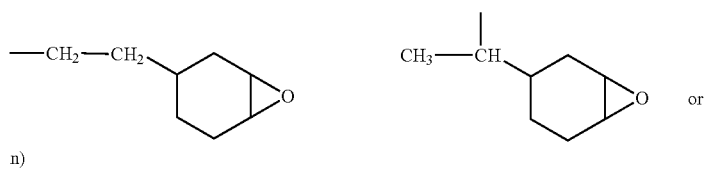
n)
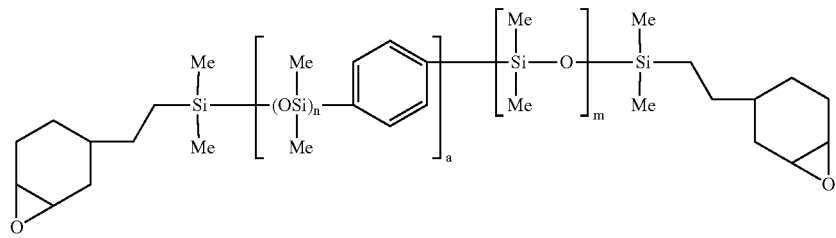
(S-14)
with n < 100; a < 100 and m < 100
o)
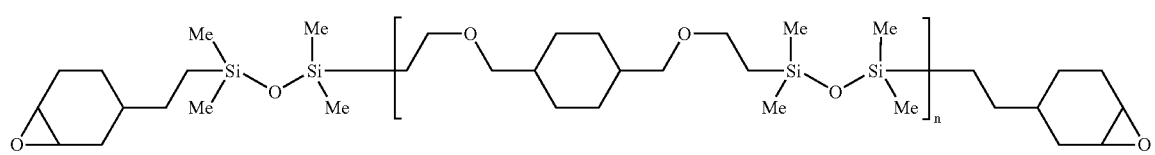
(S-15)
with n < 100
in which formulae $R°$ or $R_0$, which are identical or different, represent an alkyl, cycloalkyl or aryl radical, preferably a C1-C6 lower alkyl.

S16
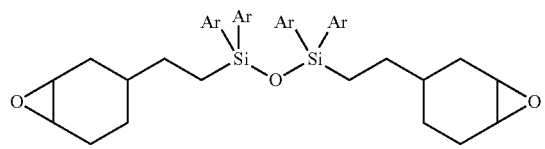
S17
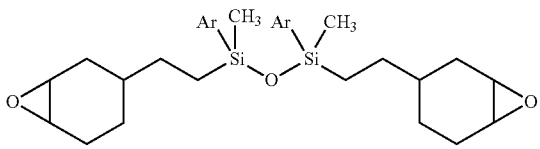
S18
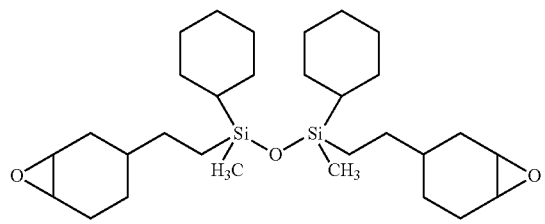
S19
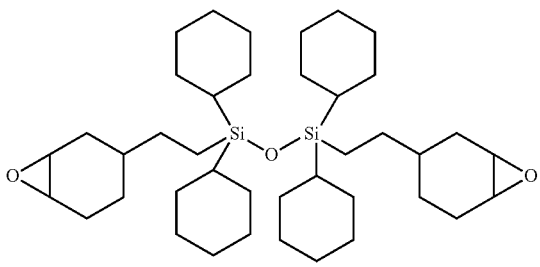
S20
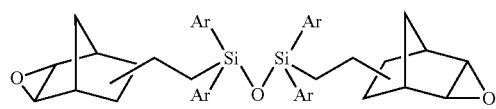
S21
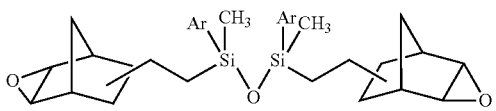
S22
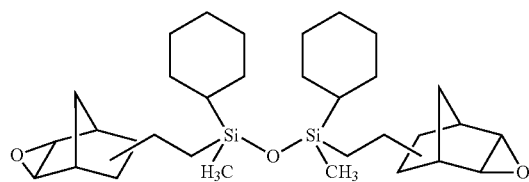
S23
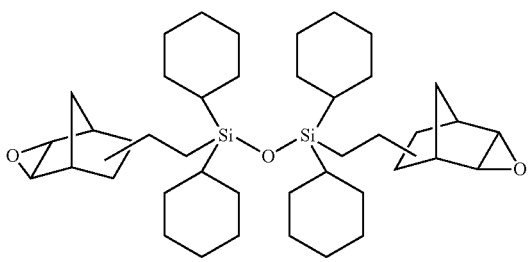
S24
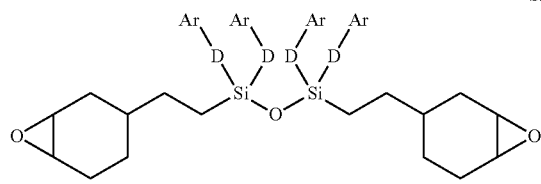
S25
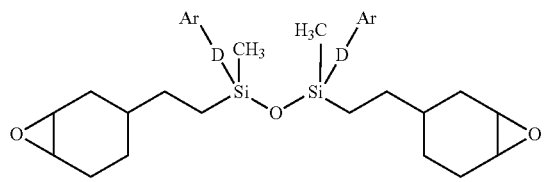
S26
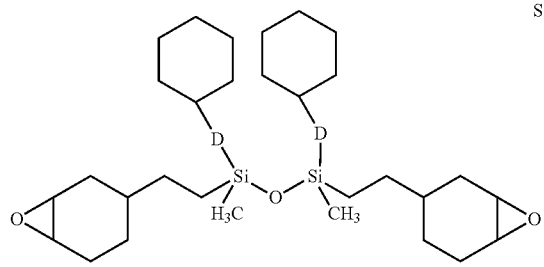
S27
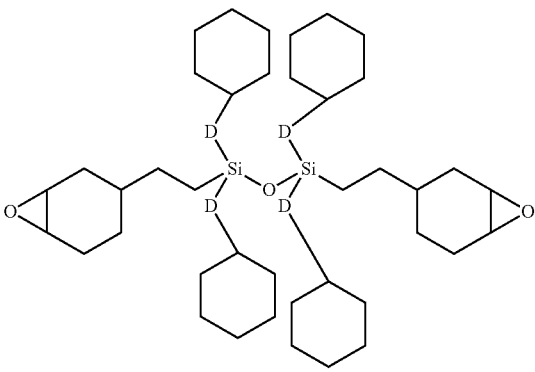

-continued
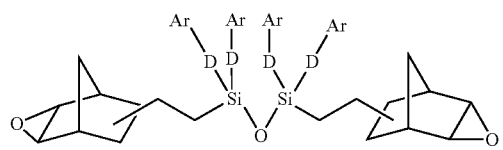
S28
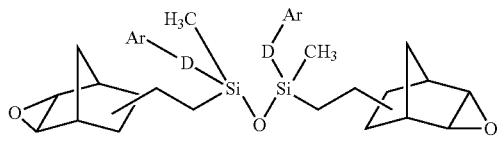
S29
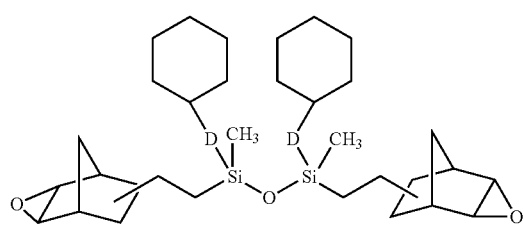
S30
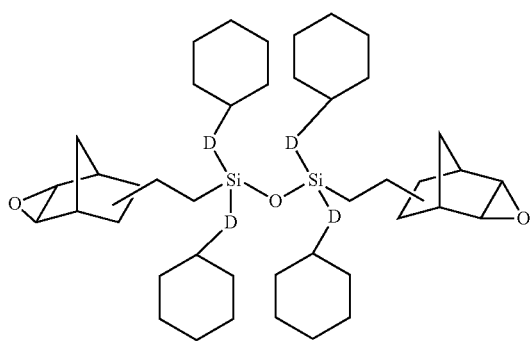
S31
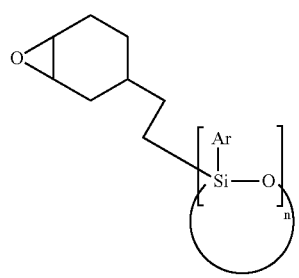
S32
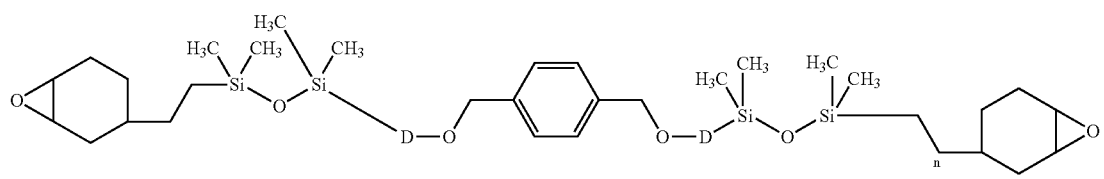
S33
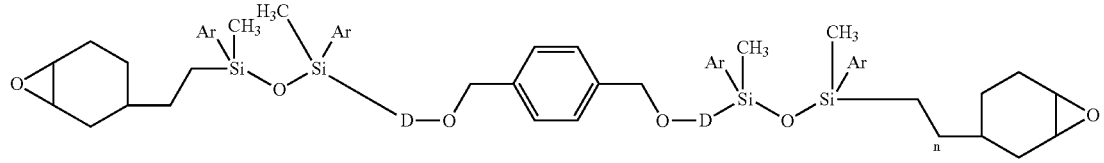
S34
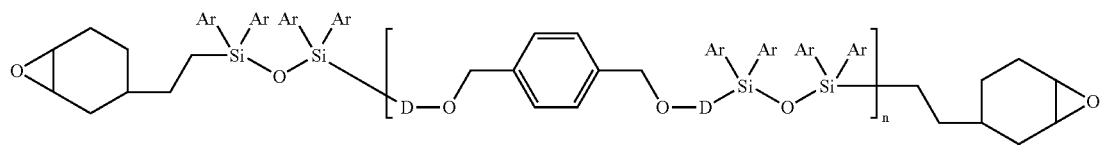
S35
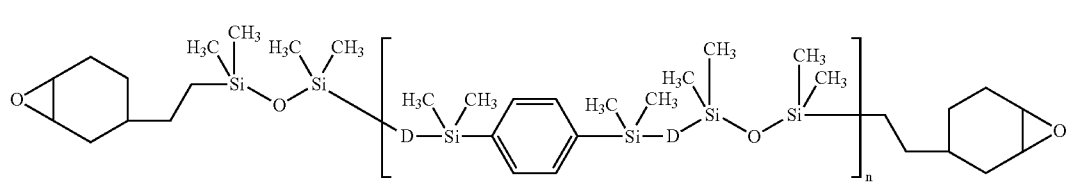
S36

-continued
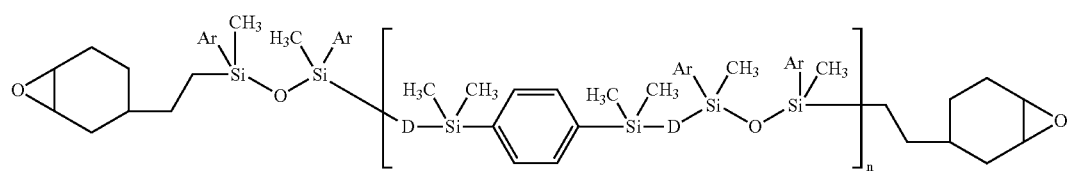
S37
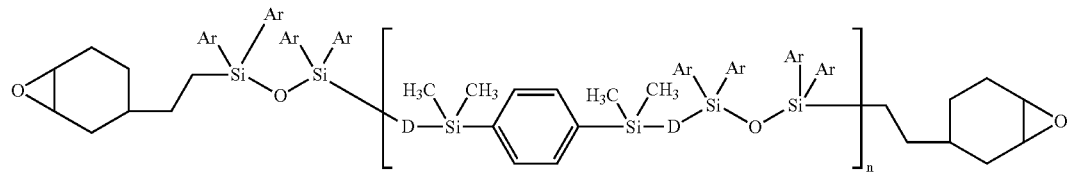
S38
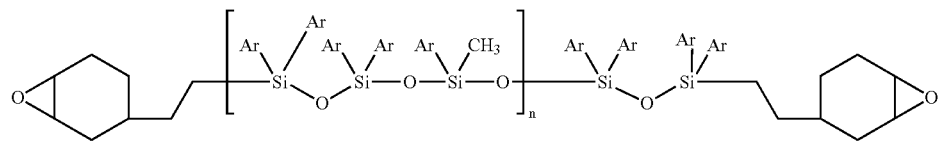
S39
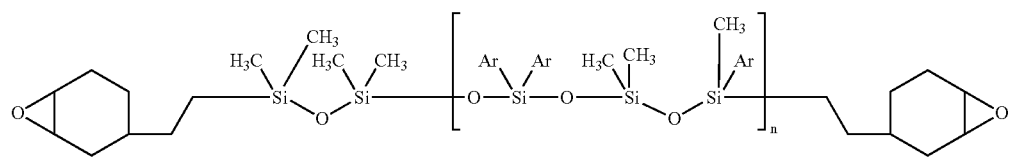
S40
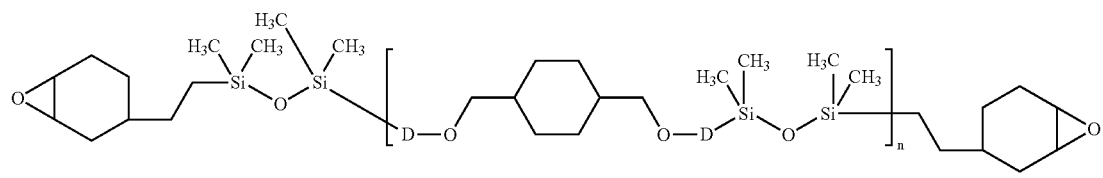
S41
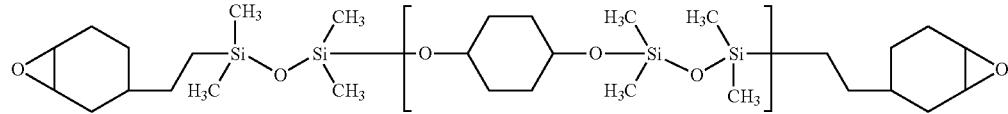
S42
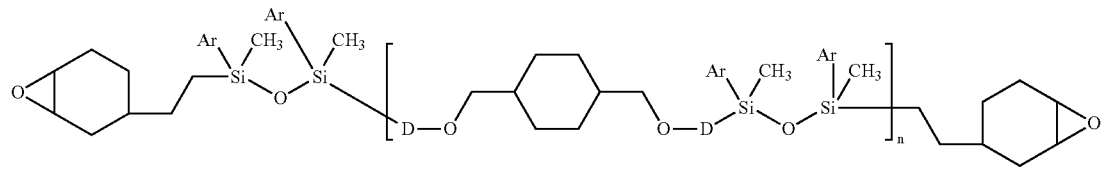
S43
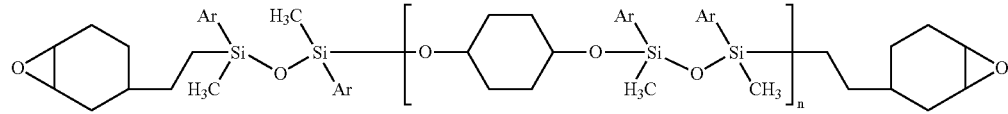
S44
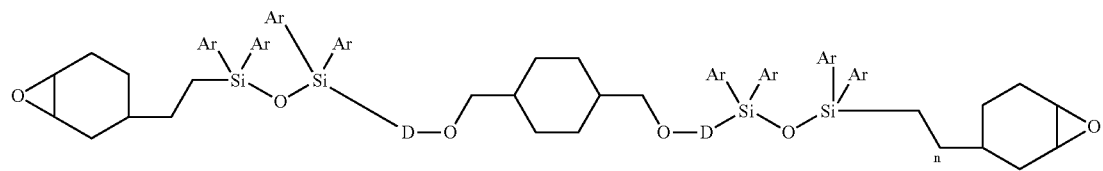
S45

-continued
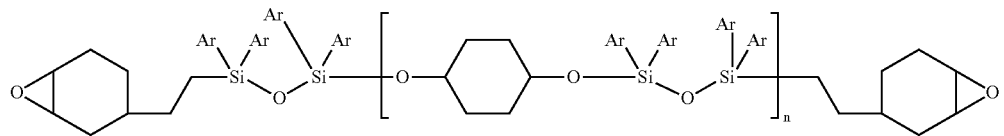
S46
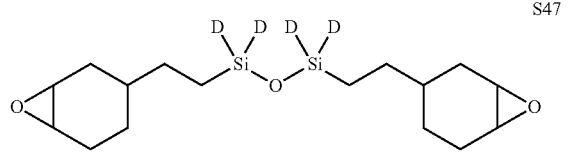
S47
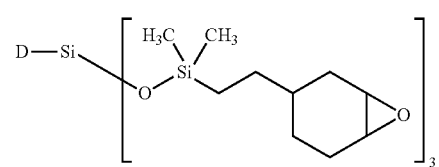
S48
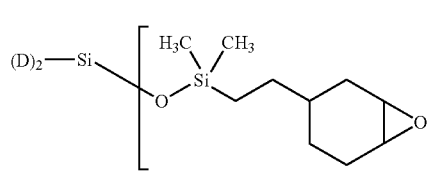
S49
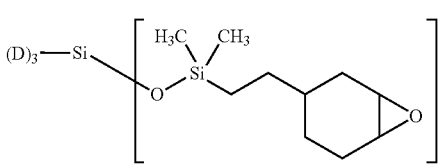
S50
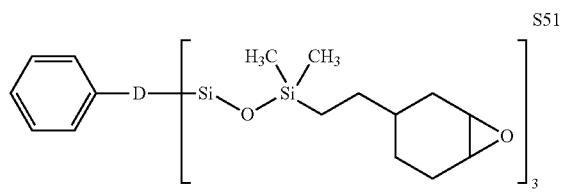
S51
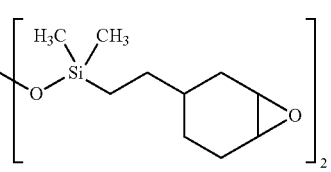
S52
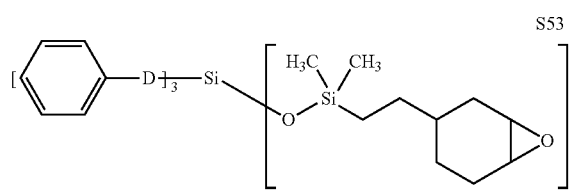
S53
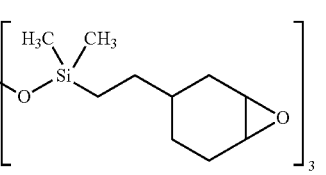
S54
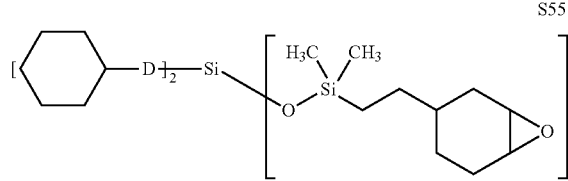
S55
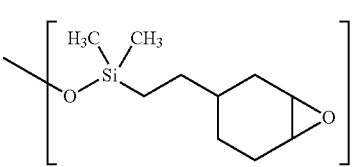
S56
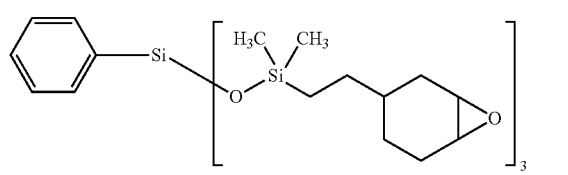
S57
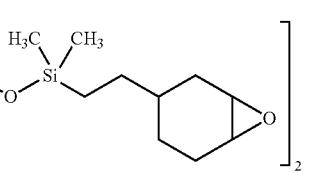
S58
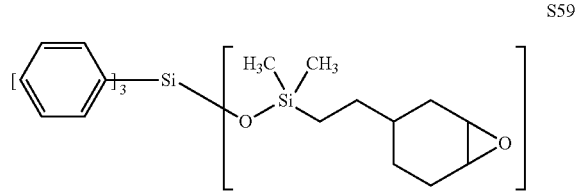
S59
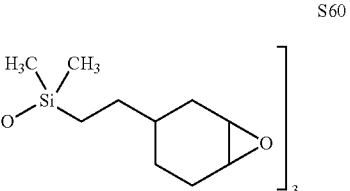
S60

-continued
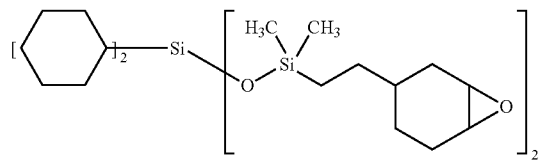
S61
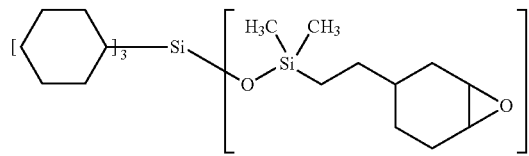
S62
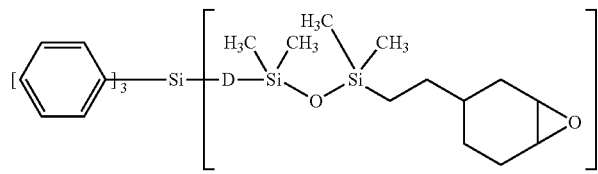
S63
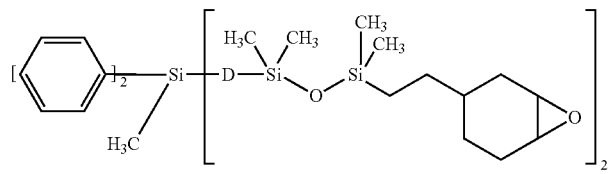
S64
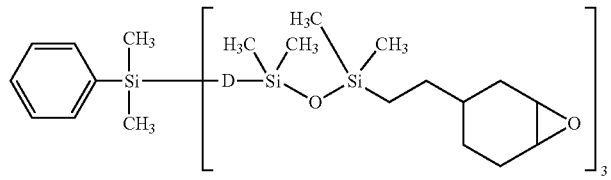
S65
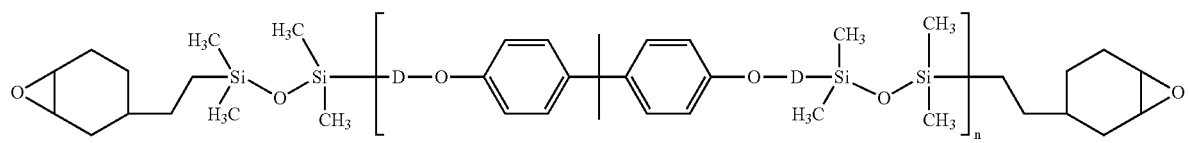
S66
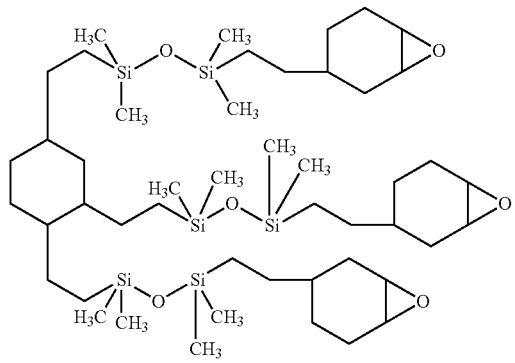
S67

-continued
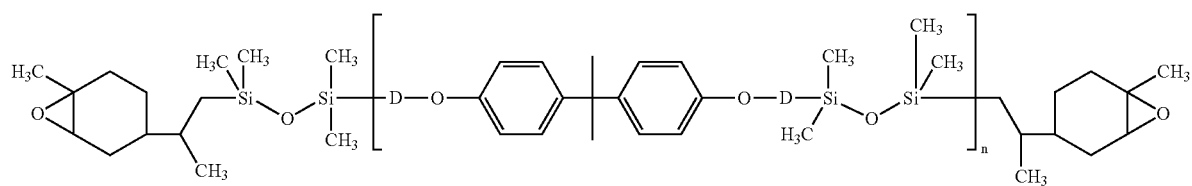
S68
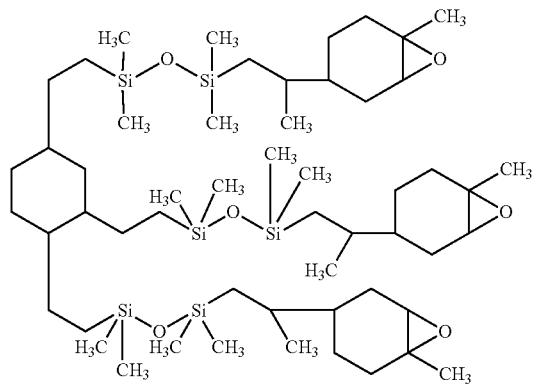
S69
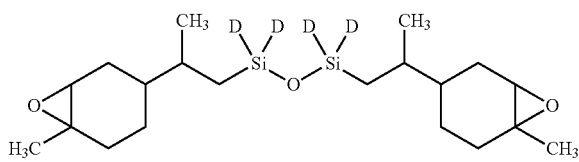
S70
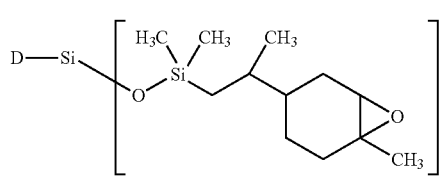
S71
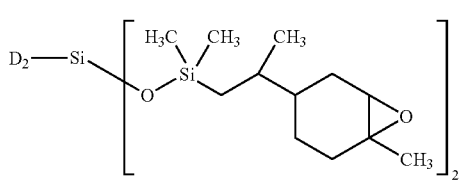
S72
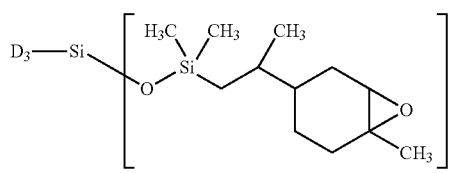
S73
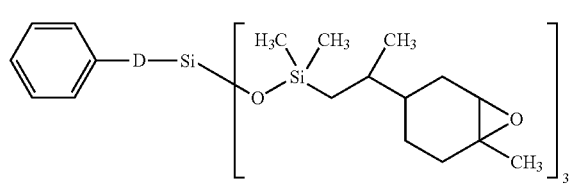
S74
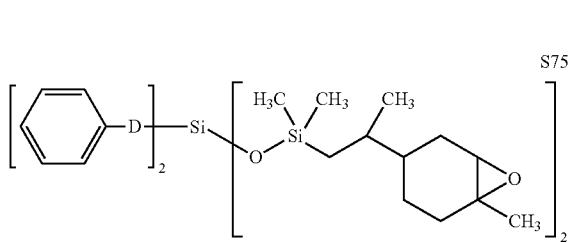
S75
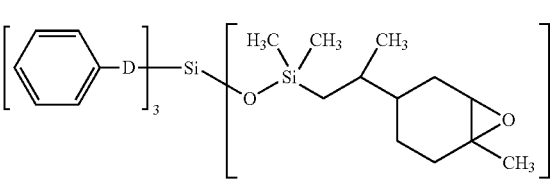
S76

-continued
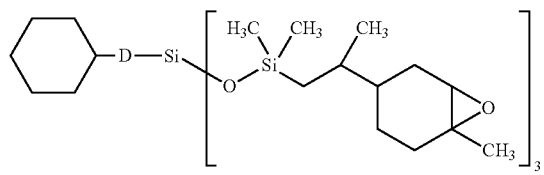
S77
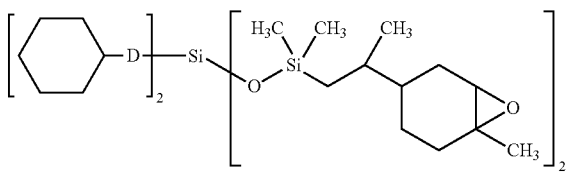
S78
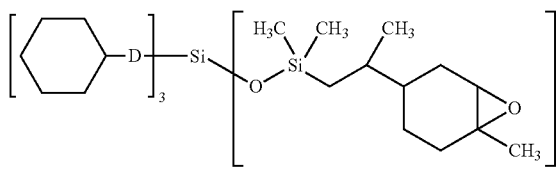
S79
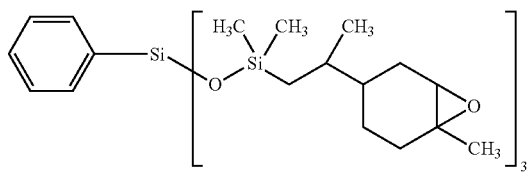
S80
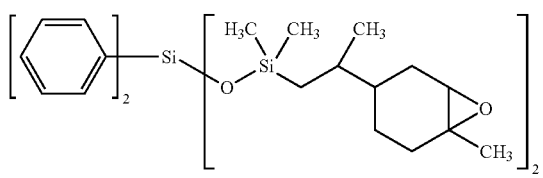
S81
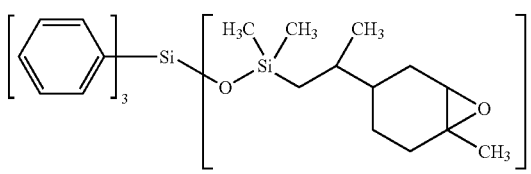
S82
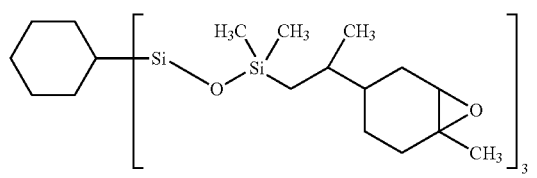
S83
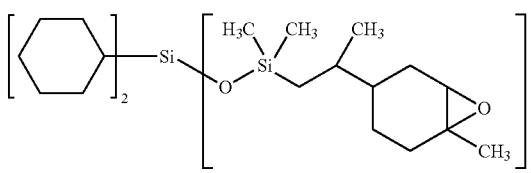
S84
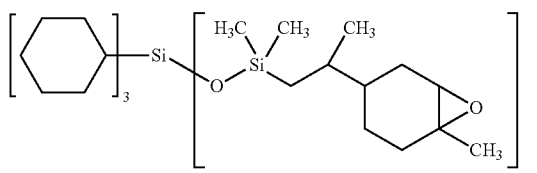
S85
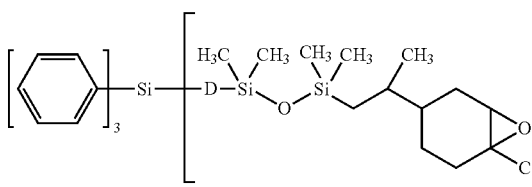
S86
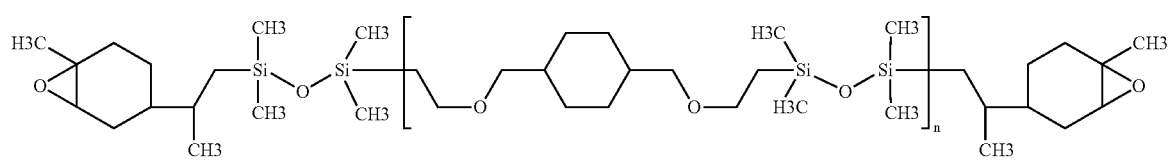
S87
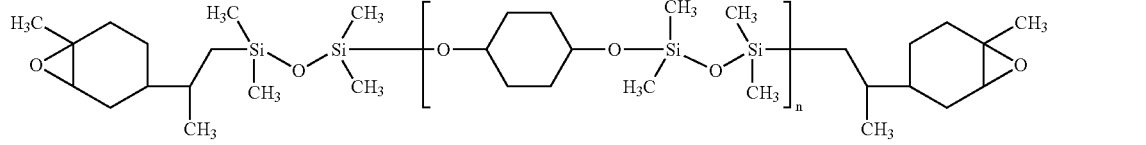
S88
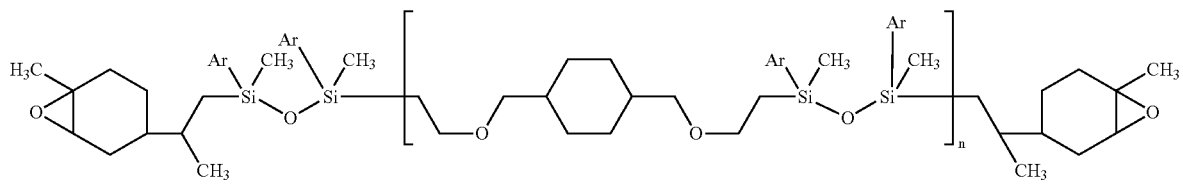
S89

-continued

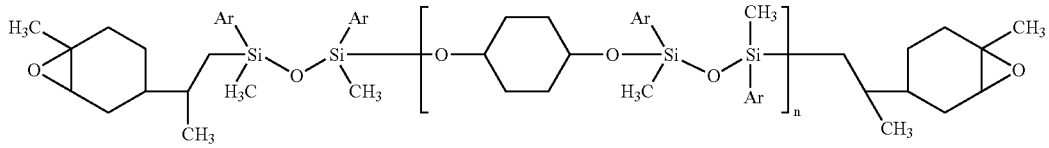
S90

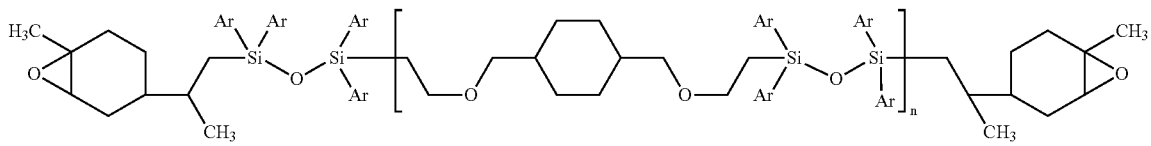
S91

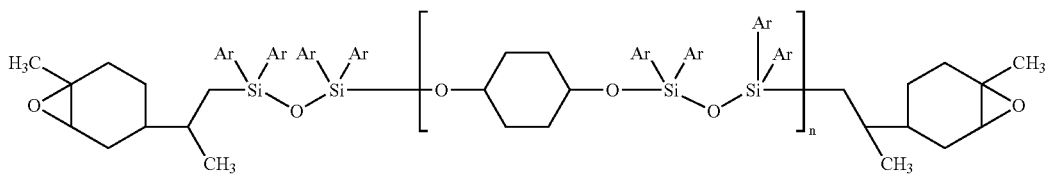
S92 in which formulae the group D is a linear or branched C1-C12 alkyl and n is an integer between 1 and 20 (inclusive), with Ar=aryl group.

According to one preferred embodiment the cationically reactive compound (A) is a silane (G-3) of formula:

$$(Z)_a-\underset{\underset{E}{|}}{\overset{(R)_b}{Si}}-E$$

in which:

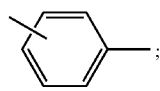

-continued

R, identical or different at each occurrence, represents an alkyl, cycloalkyl, aryl, vinyl, hydrogeno or alkoxy radical, preferably a C1-C6 lower alkyl, Z, identical or different at each occurrence, is an organic substituent containing at least one oxirane, alkenyl ether, oxetane and/or carbonate function, and a+b=3.

According to one preferred embodiment the silane (G-3) is selected from the group consisting of the molecules (S-93) to (S-95):

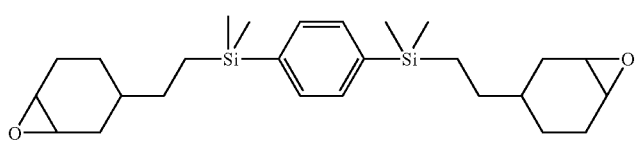
(S-93)

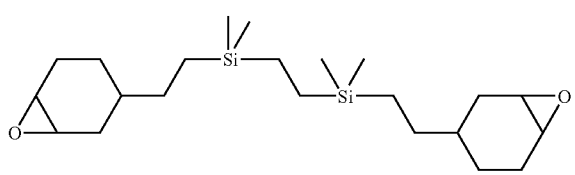
(S-94)

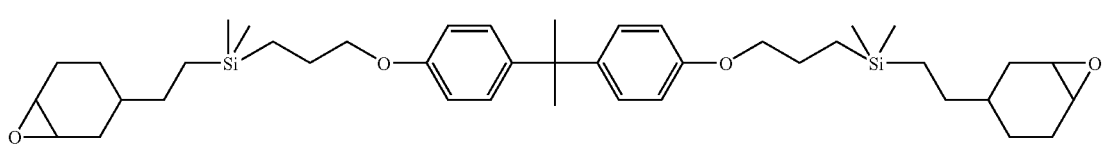
(S-95)

According to another preferential embodiment the cationically reactive compound (A) (G) is an organic compound (G-4) selected from the group consisting of the molecules (S-96) to (S-104):

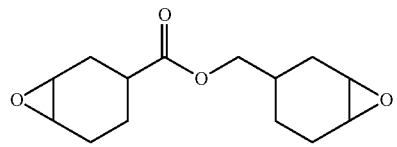
(S-96)

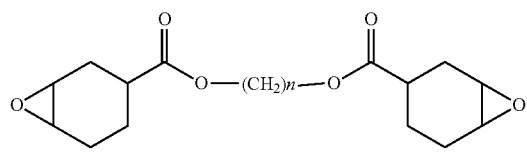
(S-97)

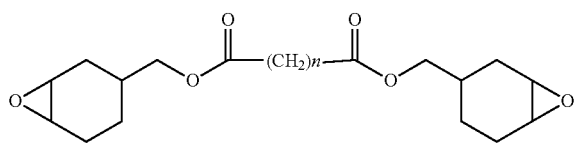
(S-98)

in which formulae n is an integer between 1 and 10 (inclusive):

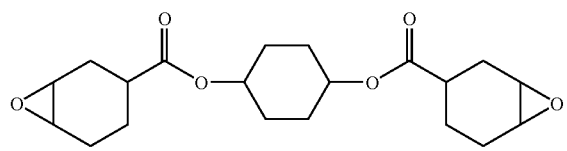
(S-99)

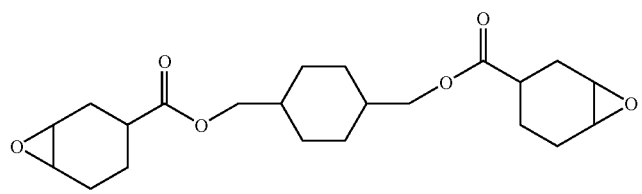
(S-100)

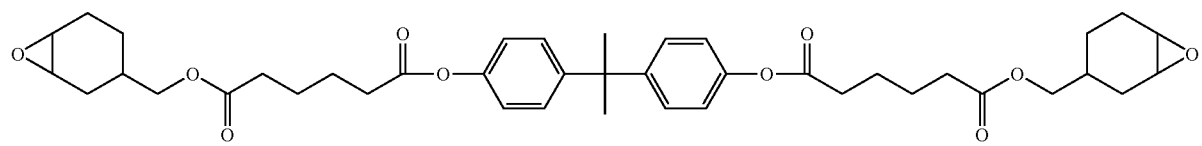
(S-101)

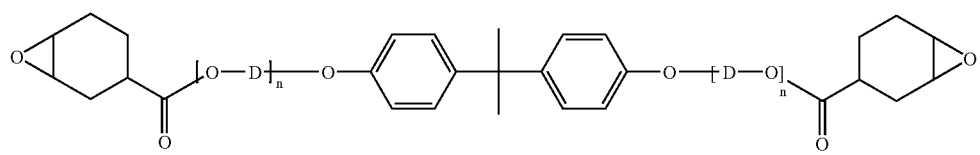
(S-103)

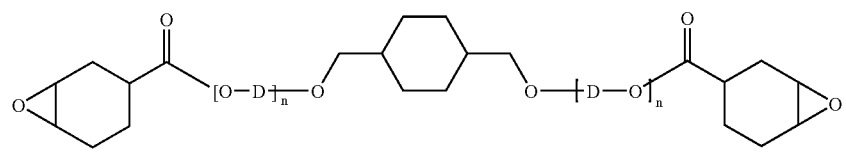
(S-104)

with n<100 and D=linear or branched $C_1$-$C_{12}$ alkyl.

Selectable molecules of type (S-103) include the resin UVR6150® sold by the company Dow Chemical; and with n<100 and the group D=linear or branched C1-C12 alkyl.

For the resins of type (S-104), that where n=0 is particularly suitable for the invention.

According to another advantageous version of the present invention, the cationically reactive compound (A) is combined with an organic epoxy or oxetane resin representing less than 80% by mass of the fraction of the silicone oligomer or polymer (A-1). Among the functional organic resins selected, preference would be given to those for which the percentage by mass of reactive function is less than 20% and preferably less than 15%. There will be a corresponding decrease in the volume contraction on polymerization.

Preference will be given to selecting the resins of formula (R-1) and (R-2)

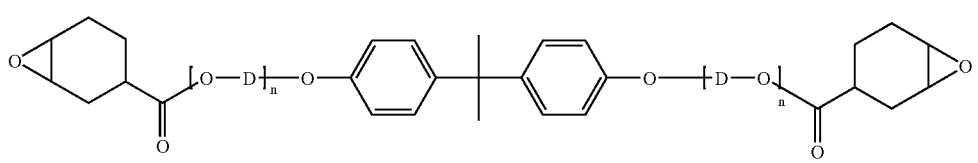

(R-1)

with n<100 and D=linear or branched C1-C12 alkyl.

Among the resins of type (R-1) it is possible to select the resin UVR6150 sold by the company Dow Chemical.

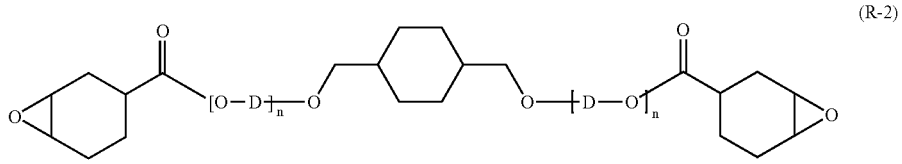

(R-2)

with n<100 and D=linear or branched C1-C12 alkyl.

Among the resins of type (R-2) it is possible to select the resin where n=0.

Different types of dental filler (B) can be used for preparing the compositions according to the invention. The fillers are selected as a function of the end use of the dental composition: they affect important properties such as appearance, penetration of UV radiation, and also mechanical and physical properties of the material obtained after crosslinking and/or polymerization of the dental composition.

As a reinforcing filler use may be made of untreated or treated pyrogenic silica fillers, amorphous silica fillers, quartz, glasses or nonvitreous fillers based on oxides of silicon, of the type for example of those described in patent U.S. Pat. No. 6,297,181 (without barium), of zirconium, of barium, of calcium, of fluorine, of aluminum, of titanium or of zinc, borosilicates, aluminosilicates, talc, Spherosil, ytterbium trifluoride, fillers based on polymers in the form of ground powder, such as inert or functionalized polymethyl methacrylates, or polyepoxides or polycarbonates, whiskers of ceramics (Si—C, Si—O—C, Si—N, Si—N—C, Si—N—C—O), and glass fibers.

The following are cited by way of example:
inert fillers based on polymethyl methacrylate LUXAS-ELF®, sold by the company UGL, which can be used in the dental field and are pigmented pink,
polydimethylsiloxane—or hexamethyldisilazane—treated fumed silica fillers with a specific surface area of 200 m²/g,
untreated fumed silica fillers (Aerosil AE200 or OX50®, sold by the company Degussa), and
glasses based on silicon oxides, barium oxide and/or strontium oxide.

According to one preferred embodiment the dental filler (B) is an inorganic glass or a fumed silica.

In accordance with one advantageous feature of the invention the dental filler (B) represents up to 85% by weight, preferably between 50 and 85% by weight, and more preferably between 60 and 85% by weight, relative to the total weight of the dental composition.

In accordance with the invention the dispersant (C) is selected from the group consisting of the following: polyurethane/acrylate copolymers optionally converted to an alkylammonium salt form, acrylic copolymers optionally converted to an alkylammonium salt form, monodiesters of carboxylic acids, polyesters, polyethers, polyurethanes, modified polyurethanes, polyol polyacrylates, copolymers thereof or mixtures thereof. The dispersants sold under the brand name Disperbyk® (from the company Byk) or Solsperse® (from the company Avecia) are particularly suitable for the invention. Mention may be made, in particular and by way of example, of the following commercial products: Disperbyk® 164, Disperbyk® 161, Disperbyk® 166, Disperbyk® 2070, Disperbyk® 9075, and Disperbyk® 9076. Mention may also be made of the dispersants cited in the following patents:

patent U.S. Pat. No. 5,882,393, describing dispersants based on polyurethane/imidazole acrylates or epoxides;
patent U.S. Pat. No. 5,425,900, describing dispersants based on polyurethanes;
patent U.S. Pat. No. 4,795,796, describing dispersants based on polyurethane/polyoxyalkylene glycol monoalkyl ethers;
patent application WO-A-99/56864, describing dispersants based on polyurethane/poly(oxy-alkylene-carbonyl)s: derived from ε-caprolactone and from δ-valerolactone; and patent EP-0 403 197, describing grafted polyol polyacrylate dispersants comprising a random polyurethane/polyvinyl/polyacrylate copolymer and a polyoxyalkylene polyether.

Quantitatively speaking, the dispersant (C) is present in a proportion of 50 ppm to 1%, preferably 100 ppm to 5000 ppm.

The amine index of the dispersant (C) is preferably less than or equal to 60 and more preferably between 0.1 and 50 mg of potassium hydroxide per gram of dispersant (C).

The acid index of the dispersant is advantageously less than or equal to 200, preferably less than or equal to 100, and more preferably between 1 and 60 mg of potassium hydroxide per gram of dispersant.

The cationic photoinitiators (D) are selected from the onium borates (individually or in a mixture) of an element from groups 15 to 17 of the Periodic Table [Chem. & Eng. News, Vol. 63, No. 5, 26, dated Feb. 4, 1985] or of an organometallic complex of an element from groups 4 to 10 of the Periodic Table [same reference].

According to one preferential embodiment the cationic photoinitiator (D) is of borate type and is selected from those for which:
a) the cationic entity of the borate is selected from:
(1) onium salts of the formula:

[(R$^1$)$_n$-A-(R$^2$)$_m$]$^+$  (VII)

in which:
A represents an element from groups 15 to 17 such as, for example: I, S, Se, P or N,
R$^1$ represents a C6-C20 heterocyclic or carbocyclic aryl radical, it being possible for said heterocyclic radical to contain nitrogen or sulfur as heteroelements,
R$^2$ represents R$^1$ or a C1-C30 linear or branched alkyl or alkenyl radical, said radicals R$^1$ and R$^2$ being optionally substituted by a C1-C25 alkoxy, C1-C25 alkyl, nitro, chloro, bromo, cyano, carboxyl, ester or mercapto group,
m and n are integers, with n+m=v+1, v being the valence of the element A,
(2) oxoisothiochromanium salts, specifically those described in patent application WO 90/11303, particularly the sulfonium salt of 2-ethyl-4-oxoisothiochromanium or of 2-dodecyl-4-oxoisothiochromanium, and the oxoisothiochromanium salts of structural formula V:

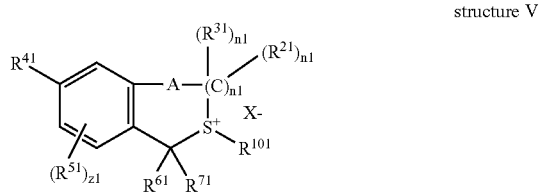

structure V in which:
A represents

n1=an integer between 1 and 3;
z1=an integer between 0 and 3;

x represents a group of formula M$^1$Y$^1$$_{r1}$ (1) or of formula Q$^1$ (2), where in M$^1$Y$^1$$_{r1}$ (1): M$^1$=Sb, As, P, B or Cl, Y$^1$ represents a halogen (preferably F or Cl) or O, and r1 is an integer between 4 and 6; the formula Q$^1$ (2) represents a sulfonic acid;
R$^{81}$-SO$_3$ where R$^{81}$ is an alkyl or aryl group, or an alkyl or aryl group substituted by a halogen, preferably F or Cl,
R$^{101}$ represents an alkyl or a cycloalkyl group, preferably C$_1$-C$_{20}$, or an aryl group,
R$^{21}$ represents a hydrogen, an alkyl, alkenyl, cycloalkenyl or cycloalkyl group, preferably C$_1$-C$_{20}$, or an aryl group, all of the R$^{21}$s being independent of one another,
R$^{31}$ represents a hydrogen, an alkyl, alkenyl, cycloalkenyl or cycloalkyl group, preferably C$_1$-C$_{20}$, or an aryl group, all of the R$^{31}$s being independent of one another,
R$^{41}$ represents a hydrogen, halogen, an alkenyl group, vinyl for example, or a cycloalkenyl, alkyl, or cycloalkyl group, preferably C$_1$-C$_{20}$, an alkoxy or thioalkoxy group, preferably C$_1$-C$_{20}$, a poly(alkylene oxide) group having up to 10 alkylene oxide units and terminated by a hydroxyl or an alkyl (C$_1$-C$_{12}$), or an aryl group, or an aryloxy or thioaryloxy group,
R$^{51}$ represents a halogen, an alkenyl group, vinyl for example, or a cycloalkenyl, alkyl, or cycloalkyl group, preferably C$_1$-C$_{20}$, an alkoxy or thioalkoxy group, preferably C$_1$-C$_{20}$, a poly(alkylene oxide) group having up to 10 alkylene oxide units and terminated by a hydroxyl or an alkyl (C$_1$-C$_{22}$), or an aryl group, or an aryloxy or thioaryloxy group,
R$^{61}$ represents a hydrogen, an alkyl, alkenyl, cycloalkenyl or cycloalkyl group, preferably C$_1$-C$_{20}$, or an aryl group,
R$^{71}$ represents a hydrogen, an alkyl, alkenyl, cycloalkenyl or cycloalkyl group, preferably C$_1$-C$_{20}$, or an aryl group; and
(3) organometallic salts of the following formula:

(L$_1$L$_2$L$_3$M)$^{+q}$  (VIII)

in which:
M represents a metal from group 4 to 10, especially iron, manganese, chromium or cobalt,
L1 represents 1 ligand bonded to the metal M by π electrons, the ligand being selected from η$^3$-alkyl, η$^5$-cyclopentadienyl and η$^7$-cycloheptatrienyl ligands and the η$^6$-aromatic compounds selected from optionally substituted η$^6$-benzene ligands and compounds having 2 to 4 fused rings, each ring being capable of contributing to the valence layer of the metal M via 3 to 8 π electrons,
L2 represents a ligand bonded to the metal M by π electrons, the ligand being selected from η$^7$-cycloheptatrienyl ligands and the η$^6$-aromatic compounds selected from optionally substituted η$^6$-benzene ligands and compounds having 2 to 4 fused rings, each ring being capable of contributing to the valence layer of the metal M via 6 or 7 π electrons,
L3 represents 0 to 3 identical or different ligands bonded to the metal M by σ electrons, the ligand(s) being selected from CO and NO2+; the total electronic charge q of the complex to which L1, L2 and L3 contribute, and the ionic charge of the metal M, being positive and being 1 or 2; and
b) the anionic borate entity has the formula:

[BX$_a$R$_b$]$^-$  (I)

in which formula:
a and b are integers ranging from 0 to 3 for a and from 1 to 4 for b, with a+b=4,
the symbols X represent:

a halogen (chlorine, fluorine) atom, with a=0 to 3, or an OH function, with a=0 to 2, the symbols R are identical or different and represent:
a phenyl radical substituted by at least one electron-withdrawing group such as, for example, $OCF_3$, $CF_3$, $NO_2$ or CN and/or by at least two halogen atoms (especially fluorine), when the cationic entity is an onium of an element from groups 15 to 17, a phenyl radical substituted by at least one electron-withdrawing element or group, in particular a halogen atom (especially fluorine), $CF_3$, $OCF_3$, $NO_2$ or CN, when the cationic entity is an organometallic complex of an element from groups 4 to 10, or an aryl radical containing at least two aromatic nuclei, such as, for example, biphenyl, naphthyl, optionally substituted by at least one electron-withdrawing element or group, in particular a halogen atom, especially fluorine, $OCF_3$, $CF_3$, $NO_2$ or CN, irrespective of the cationic entity.

According to one preferred embodiment the cationic photoinitiator (D) is an iodonium salt.

Without any limitative effect, there now follow further details regarding the subclasses of onium borate and of organometallic-salt borate that are more particularly preferred in the context of the use in accordance with the invention.

According to a first preferred version of the invention the especially suitable species of the anionic borate entity are the following:

1': $[B(C_6F_5)_4]^-$   5': $[B(C_6H_3(CF_3)_2)_4]^-$
2': $[(C_6F_5)_2BF_2]^-$   6': $[B(C_6H_3F_2)_4]^-$
3': $[B(C_6H_4CF_3)_4]^-$ 7': $[C_6F_5BF_3]^-$
4': $[B(C_6F_4OCF_3)_4]^-$

According to a second preferred version of the invention the onium salts of formula (VII) that can be used are described in numerous documents, and particularly in patents U.S. Pat. Nos. 4,026,705, 4,032,673, 4,069,056, 4,136,102, and 4,173,476.

Among these salts, particular privilege will be given to the following cations:

$[(C_8H_{17})\text{-}O\text{-}(C_6H_4)\text{-}I\text{-}C_6H_5)]^+$; $[C_{12}H_{25}\text{-}(C_6H_4)\text{-}I\text{-}C_6H_5]^+$;
$[(C_8H_{17}\text{-}O\text{-}(C_6H_4))_2I]^+$
$[(C_8H_{17})\text{-}O\text{-} \quad (C_6H_4)\text{-}I\text{-}C_6H_5)]^+$; $[(C_6H_5)_2S\text{-}(C_6H_4)\text{-}O\text{-}C_8H_{17}]^+$;
$[CH_3\text{-}C_6H_4\text{-}I\text{-}C_6H_4\text{-}CH_2CH(CH_3)_2]^+$;
$[(C_{12}H_{25}\text{-}(C_6H_4)\text{-}I\text{-}(C_6H_4)\text{-}CH\text{-}(CH_3)_2]^+$;
$[(C_{12}H_{25}\text{-}C_6H_4)_2I]^+$;
$[(C_6H_5)_3S]^+$;
$[CH_3\text{-}(C_6H_4)\text{-}I\text{-}(C_6H_4)\text{-}CH(CH_3)_2]^+$
$(\eta 5\text{-cyclopentadienyl}) (\eta 6\text{-toluene})Fe^+$;
$(\eta 5\text{-cyclopentadienyl}) (\eta 6\text{-cumene})Fe^+$;
$(\eta 5\text{-cyclopentadienyl}) (\eta 6\text{-1-methylnaphthalene})Fe^+$;
$[(C_6H_5)\text{-}S\text{-}C_6H_4\text{-}S\text{-}(C_6H_5)_2]^+$; $[(CH_3\text{-}(C_6H_4)\text{-}I\text{-}(C_6H_4)\text{-}OC_2H_5]^+$;
$[(C_nH_{2n+1}\text{-}C_6H_4)_2I]^+$ with n=1 to 18.

According to a third preferred version, the organometallic salts (3) of formula (VIII) that can be used are described in documents U.S. Pat. No. 4,973,722, U.S. Pat. No. 4,992,572, EP-A-203 829, EP-A-323 584, and EP-A-354 181. The organometallic salts more readily employed according to the invention are in particular:

$(\eta^5\text{-cyclopentadienyl}) (\eta^6\text{-toluene})Fe^+$,
$(\eta^5\text{-cyclopentadienyl}) (\eta^6\text{-1-methylnaphthalene})Fe^+$,
$(\eta^5\text{-cyclopentadienyl}) (\eta^6\text{-cumene})Fe^+$,
$bis(\eta^6\text{-mesitylene})Fe^+$,
$bis(\eta^6\text{-benzene})Cr^+$.

In accord with these three preferred versions mention may be made, as examples of onium borate photoinitiators, of the following products:

(P-16): $[(C_8H_{17})\text{-}O\text{-}C_6H_4\text{-}I\text{-}C_6H_5)]^+$, $[B(C_6F_5)_4]^-$;
(P-17): $[C_{12}H_{25}\text{-}C_6H_4\text{-}I\text{-}C_6H_5]^+$, $[B(C_6F_5)_4]^-$;
(P-18): $[(C_8H_{17}\text{-}O\text{-}C_6H_4)_2I]^+$, $[B(C_6F_5)_4]^-$;
(P-19): $[(C_8H_{17})\text{-}O\text{-}C_6H_4\text{-}I\text{-}C_6H_5)]^+$, $[B(C_6F_5)_4]^-$;
(P-20): $[(C_6H_5)_2S\text{-}C_6H_4\text{-}O\text{-}C_8H_{17}]^+$, $[B(C_6H_4CF_3)_4]^-$;
(P-21): $[(C_{12}H_{25}\text{-}C_6H_4)_2I]^+$, $[B(C_6F_5)_4]^-$;
(P-22): $[CH_3\text{-}C_6H_4\text{-}I\text{-}C_6H_4\text{-}CH(CH_3)_2]^+$, $[B(C_6F_5)_4]^-$;
(P-23): $(\eta 5\text{-cyclopentadienyl})(\eta 6\text{-toluene})Fe^+$, $[B(C_6F_5)_4]^-$;
(P-24): $(\eta 5\text{-cyclopentadienyl})(\eta 6\text{-1-methylnaphthalene})Fe^+$, $[B(C_6F_5)_4]^-$;
(P-25): $(\eta 5\text{-cyclopentadienyl})(\eta 6\text{-cumene})Fe^+$, $[B(C_6F_5)_4]^-$;
(P-26): $[C_{12}H_{25}\text{-}C_6H_4)_2I]^+$, $[B(C_6H_3(CF_3)_2]^-$;
(P-27): $[CH_3\text{-}C_6H_4\text{-}I\text{-}C_6H_4\text{-}CH_2CH(CH_3)_2]^+$, $[B(C_6F_5)_4]^-$;
(P-28): $[CH_3\text{-}C_6H_4\text{-}I\text{-}C_6H_4\text{-}CH_2CH(CH_3)_2]^+$, $[B(C_6H_3(CF_3)_2)_4]^-$; and
(P-29): $[CH_3\text{-}C_6H_4\text{-}I\text{-}C_6H_4\text{-}CH(CH_3)_2]^+$, $[B(C_6H_3(CF_3)_2)_4]^-$.

As other reference for defining the onium borates (1) and (2) and the organometallic-salt borates (3), mention may be made of the entirety of the content of patent applications EP 0 562 897 and 0 562 922.

As further example of onium salt which can be used as photoinitiator, mention may be made of those disclosed in US patents U.S. Pat. No. 4,138,255 and U.S. Pat. No. 4,310,469.

Use may also be made of other cationic photoinitiators, for example:

hexafluorophosphate or hexafluoroantimonate iodonium salts, such as:
$[CH_3\text{-}[(C_6H_4)\text{-}I\text{-}[(C_6H_4)\text{-}CH(CH_3)_2]^+$, $[PF_6]^-$;
$[CH_3\text{-}(C_6H_4)\text{-}I\text{-}(C_6H_4)\text{-}CH_2CH(CH_3)_2]^+$, $[PF_6]^-$;
$[(C_{12}H_{25}\text{-}C_6H_4)_2I]^+$, $[PF_6]^-$; or
the ferrocenium salts of these various anions.

In the context of the invention, the material obtained after crosslinking exhibits color stability, good mechanical properties, good elasticity, and good compressive strength.

Besides the reinforcing fillers, pigments may be used to color the dental composition in accordance with the intended use and ethnic groups.

For example, red pigments are used in the presence of microfibers for the dental compositions used for preparing dental prostheses, in order to simulate blood vessels.

Use is also made of pigments based on metal oxides (iron oxides and/or titanium oxide and/or aluminum oxide and/or zirconium oxide, etc.) for the dental compositions used for preparing restoration material, so as to give an ivory-colored crosslinked material.

Other additives may be incorporated into dental compositions according to the invention. Examples include biocides, stabilizers, flavors, plasticizers, and adhesion promoters.

Among the additives that may be considered, use will be made advantageously of organic coreactants which are crosslinkable and/or polymerizable. These coreactants are liquid at ambient temperature or thermofusible at a temperature lower than 100° C., and each coreactant comprises at least two reactive functions such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyl, dioxolane-dioxolane-alcohol, etc.

The dental compositions according to the invention may be used for numerous dental applications, and especially in the field of dental prostheses, in the field of dental restoration, and in the field of temporary teeth.

The dental composition according to the invention is preferably in the form of a single product comprising the various components ("monocomponent"), thereby facilitating its employment, particularly in the field of dental prostheses. If appropriate the stability of this product may be ensured by means of amine-functional organic derivatives in accordance with the teaching of document WO 98/07798.

In the field of dental prostheses, the product in the "mono-component" form may be deposited with the aid of a syringe directly on the plaster model or in a core. It is then polymerized (polymerization by possible successive layers) with the aid of a UV lamp (visible light spectrum 200-500 nm).

In general it is possible to produce an esthetic and durable dental prosthesis in 10 to 15 minutes.

It should be noted that the products obtained from the dental composition according to the invention are nonporous. Hence, after optional polishing with the aid of a felt brush, for example, the surface of the dental prostheses obtained is smooth and bright and therefore does not require the use of varnish.

The applications in the field of dental prostheses are essentially those of the attached prosthesis, and can be divided into two types:
total prosthesis in the case of a patient with no teeth at all;
partial prosthesis owing to the absence of several teeth, resulting either in a temporary prosthesis or in a skeleton brace.

In the field of dental restoration, the dental composition according to the invention may be used as material for filling the anterior and posterior teeth in different colors (for example, "VITA" colors), and is rapid and easy to use.

Since the dental composition is nontoxic and can be polymerized in thick layers, it is not essential to polymerize the material in successive layers. In general a single injection of the dental composition is sufficient.

The preparations for dental prostheses and for restoration materials are carried out according to the usual techniques of the art.

In the case of application of the dental composition to a tooth, either the tooth may be pretreated with a mordant and then with a bonding primer, which may itself be photo-crosslinkable, or else the dental composition may be prepared as a mixture with a bonding primer prior to its use.

The examples and tests below are given by way of illustration. They make it possible in particular to understand the invention more clearly and to highlight some of its advantages and to illustrate a number of its embodiment versions.

EXAMPLES AND TEST a) Structures (S-1)

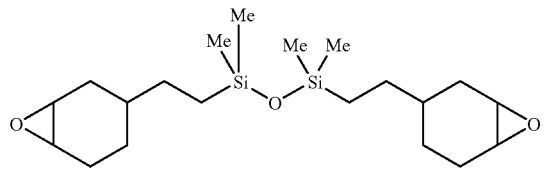

-continued

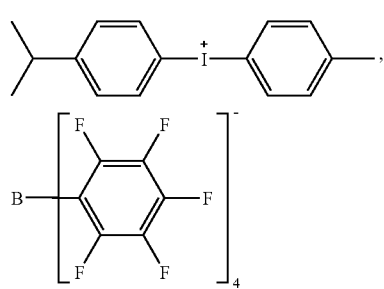
(P-27)

Definition:

The total color difference ΔE represents the change which is due not to the lightness but to the color changes that are expressed as rectangular coordinates a* and b* with the aid of a spectrocolorimeter (CIELAB model).

$\Delta a$ is termed the red-green chromatic shift.

$\Delta b$ is termed the yellow-blue chromatic shift.

If $\Delta a$ is positive, the shade is more red.

If $\Delta a$ is negative, the shade is more green.

If $\Delta b$ is positive, the shade is more yellow.

If $\Delta b$ is negative, the shade is more blue.

The chromatic shift or chromaticity difference $\Delta c$ is expressed by the relationship $$\Delta c = [(\Delta a)^2 + (\Delta b)^2]^{1/2}.$$

The values of a* measured for 144 composites were reported by Inokoshi in 1996 (Bologna International Symposium) and range between −5 and +4 and more specifically between −1 and +1. Arbitrarily, a low chromatic shift is defined when $\Delta c$ is <3 between an initial measurement made ¼ hour after crosslinking and 5 days after crosslinking and storage in the dark. The composite is photocrosslinked over a thickness of 2 mm.

b) The glasses used are glasses sold by the company Schott under the reference G018-163 or G018-066, containing or not containing a radiopacifier based on strontium oxide with particle sizes of 0.7 μm, 1.5 μm or 3.5 μm and untreated or treated with glycidyloxy-trimethoxysilane or with γ-methacryloy-loxypropyl-trimethoxysilane.

The examples presented below describe the benefit obtained by switching from a conventional thioxanthone as described in our patent application WO00/19967 to a thioxanthone substituted by at least one ammonium function, according to the invention.

Preparation of a thioxanthone containing ammonium borate functionality, compound (V):

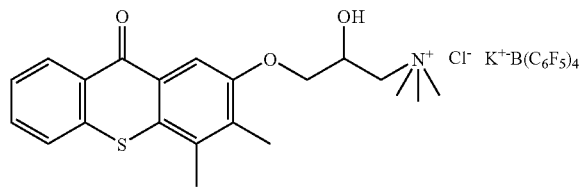

(IX)

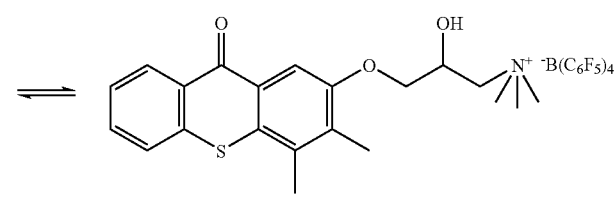

(V)

An opaque flask is charged in the absence of light with 1.02 g of 3-(3,4-dimethyl-9-oxo-9H-thioxanthen-2-yloxy)-2-hydroxypropyl) trimethylammonium chloride (sold by the company Aldrich), 2.688 g of "Kisbore" salt $KB(C_6F_5)_4$ (sold by the company Rhodia) and 50 ml of isopropanol and this initial charge is left with magnetic stirring at ambient temperature for 48 hours. The mixture is subsequently run into demineralized water (200 ml). A yellow precipitate is formed. The suspension is filtered on a commercial Büchner funnel and the solid is dried in an oven at 100° C. for 24 h. This gives the salt termed (V) (melting point 235° C.; absorption maximum λmax=397.3 nm).

Preparation of a thioxanthone containing ammonium borate functionality (VI)

An opaque flask is charged in the absence of light with 1.05 g of 3-(3,4-dimethyl-9-oxo-9H-thioxanthen-2-yloxy)-2hydroxypropyl)trimethylammonium chloride (Aldrich), 2.25 g of potassium tetrakis(3,5 trifluoro-methylphenyl)borate salt (Aldrich) and 50 ml of isopropanol and this initial charge is left with magnetic stirring at ambient temperature for 48 hours. The mixture is subsequently run into demineralized water (200 ml). A yellow precipitate is formed. The suspension is filtered on a commercial Buchner funnel and the solid is dried in an oven at 100° C. for 24 h. This gives the salt termed (VI) (melting point 230° C.; absorption maximum λmax=395 nm).

Example 1

Preparation Of A Control Formulation 1

A Hauschild centrifugal mixer is charged with 5 g of siloxane resin having a monomer (S-1) content >90% and obtained by hydrosilylation of vinylcyclohexene oxide and with 0.6 g of a 4% solution of Disperbyk164® dispersant in this resin (S-1); 0.625 g of photoinitiator system in (S-1), containing 30% of photoinitiator (P-27) and 0.23% of photosensitizer based on chloropropoxythioxanthone (CPTX), sold by the company Lambson, is added, all in solution in the resin (S-1) without solvent.

This initial charge is stirred with the centrifugal mixer at 3000 rpm at ambient temperature for 16 s and then 13.25 g of quartz (particle size 1.5 μm, sold by the company Schott under the reference G018-163 UF1.5 and treated with 2% of glycidyltrimethoxysilane) are added. The mixture is stirred with the centrifugal mixer at 3000 rpm for 16 s and 1.5 g of ytterbium trifluoride are added.

Stirring is repeated with the centrifugal mixer at 3000 rpm for 16 s and then 1.5 g of fumed silica ($SiO_2$>99%) sold by the company Degussa under the reference OX50®, are added, followed by stirring for 16 s. Finally, 2.5 g of fumed silica sold by the company Degussa under the reference R202® are added. Stirring with the centrifugal mixer is carried out for 16 s.

The formulations crosslink over a thickness of 2 to 2.5 mm with an irradiation time which is dependent on the thioxanthone used, using an Optilux Demetron lamp, this time being generally between 30 s and 1 minute.

With the aid of a Minolta CR200 colorimeter or chromameter, the L*, a* and b* values are measured after ¼ hours after crosslinking against a white background and after 5 days after crosslinking. The resulting chromatic shift Δc is deduced from these measurements: $\Delta c = [(\Delta a)^2 + (\Delta b)^2]^{1/2}$ Example 2

Preparation of a Formulation According to the Invention:

The experiment of example 1 is repeated, replacing the control thioxanthone by thioxanthones (IX) and (V), alone or in combination with the following derivatives:

9,10-dibutoxyanthracene (PS-39), phenanthrenequinone (PS-33), and camphorquinone (PS-34).

A control formulation based on compounds (PS-34) and (PS-39) is also formulated.

In examples 2e to 2h, the 3.5-micron G018-066 filler is replaced by a G018-163 glass treated with GLYMO (2.5%) and then by the resin (S-1) at 5%.

The results are set out in table I.

TABLE I

| Example | Photo-sensitizer (s) | Concentration (s) ppm | T = 1/4 hour; L a, b | | | T = 5 d; L, a, b | | | Δc |
|---|---|---|---|---|---|---|---|---|---|
| | | | L* | a* | b* | L* | a* | b* | |
| 1a (comparative) | CPTX | 60 | 72.3 | 4.7 | 3.9 | 76.6 | 1.97 | 6.36 | 3.65 |
| 2a (inventive) | (IX) | 80 | 76.5 | 0.96 | 10.6 | 79.3 | −0.13 | 10.4 | 1.1 |
| 2b (inventive) | (IX) | 220 | 74.5 | 4.14 | 14.3 | 76.7 | 3.2 | 15.3 | 1.37 |
| 2c (inventive) | (V) | 220 | 77.7 | 0.98 | 12.4 | 80.4 | −0.31 | 11.9 | 1.38 |
| 2d (inventive) | (V) | 170 | 78.8 | 0.50 | 9.3 | 80.3 | −0.8 | 8.73 | 1.42 |
| 2e (inventive) | (V); (PS-39) | 170; 130 | 73.4 | 0.46 | 14.16 | 76.47 | −1.0 | 13.04 | 1.84 |
| 2f (inventive) | (V); (PS-34); (PS-39) | 170; 100; 120 | 70.1 | −0.21 | 15.68 | 73.69 | −1.33 | 13.94 | 2.07 |
| 2g (inventive) | (V); (PS-33); (PS-39) | 170; 50; 110 | 69.08 | 1.41 | 15.58 | 73.42 | −0.79 | 15.07 | 2.26 |
| 2h (comparative) | (PS-34); (PS-39) | 100; 160 | Kinetics insufficient for crosslinking over 3 mm in 1 minute | | | | | | |

It is observed that the crosslinking with a Demetron Optilux 500 dentist's lamp of dental compositions formulated with the photosensitizers (V) or (IX), alone or in combination with other photosensitizers, for example (PS-39), (PS-34) or (PS-33), does not give rise to any coloration defect (no phenomenon of pinking during irradiation, with a low chromatic value a immediately after irradiation). A similar improvement is observed when a thioxanthone of formula (VI) is used.

The use of a thioxanthone (V), (VI) or (IX) according to the invention makes it possible to avoid the coloration problems but also the kinetic problems which are encountered using solely camphorquinone (S-34) in combination with the anthracene derivative (PS-39) (comparative exemple 2).

It is thereby shown that thioxanthones containing ammonium functionality give rise to an increased coloring stability. An initial pink color change is observed with the comparative composition of example 1 (CPTX), even at a low level of 60 ppm, which attenuates over time but which is still measurable after 5 days (a*=1.97), in contrast to the use of thioxanthones containing ammonium functionality, which do not give rise to this coloration defect at a low level and which, surprisingly, make it possible to preserve a greater color stability.

The invention claimed is:

1. A dental composition photocurable by radiation with a wavelength greater than 390 nm, the dental composition comprising:
   (1) at least one cationically reactive compound (A);
   (2) at least one dental filler (B);
   (3) optionally at least one dispersant (C) comprising at least one organic polymer or copolymer;
   (4) at least one cationic photoinitiator (D); and
   (5) at least one photosensitizer (E) which is a thioxanthone salt substituted by at least one group G containing an ammonium function, the said photosensitizer (E), optionally in combination with at least one camphorquinone, phenanthrenequinone and/or substituted anthracene, has the formula:

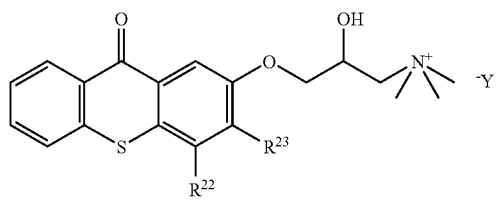

(IV)

in which:
   $R^{22}$ and $R^{23}$ are identical or different and represent a hydrogen or an optionally substituted $C_1$-$C_{10}$ alkyl radical;
   ($Y^-$) being an anionic entity, selected from the group consisting of: $BF_4^-$, $PF_6^-$; $SbF_6^-$; the anion (I) of formula $[BX_aR_b]^-$ defined below, $R_fSO_3^-$; $(R_fSO_2)_3C^-$ or $(R_fSO_2)_2N^-$, where $R_f$ is a linear or branched alkyl radical substituted by at least one halogen atom the said anion (I) of formula $[BX_aR_b]^-$ being defined in the following manner:
   a and b are integers ranging from 0 to 3 for a and from 1 to 4 for b, with a+b=4,
   the symbols X represent:
      a halogen atom, with a=0 to 3, or
      an OH function, with a=0 to 2,
   the symbols R are identical or different and represent:
      a phenyl radical substituted by at least one electron-withdrawing group and/or by at least two halogen atoms, when the cationic entity is an onium of an element from groups 15 to 17, a phenyl radical substituted by at least one electron-withdrawing element or group, when the cationic entity is an organometallic complex of an element from groups 4 to 10, or
an aryl radical containing at least two aromatic nuclei, substituted by at least one electron-withdrawing element or group, irrespective of the cationic entity.

2. The dental composition according to claim 1, wherein the photosensitizer (E), optionally in combination with at least one camphorquinone, phenanthrenequinone and/or substituted anthracene, has the formula:

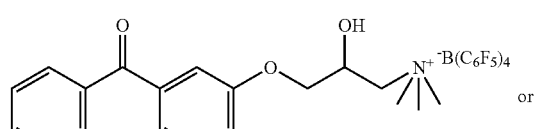

(V)

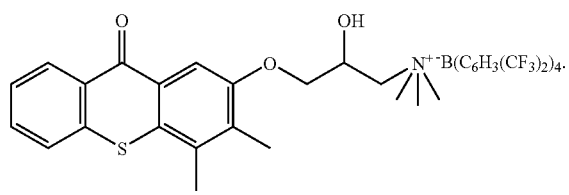

(VI)

3. The dental composition according to claim 1, wherein the photosensitizer (E) and the cationic photoinitiator (D) have the same anion.

4. The dental composition according to claim 1, wherein the cationic photoinitiator (D) is a borate and is selected from the group consisting of the following:
   a) the cationic entity of the borate is selected from:
      (1) onium salts of the formula:

$[(R^1)_n\text{-}A\text{-}(R^2)_m]^+$ (VII)

in which:
      A represents an element from groups 15 to 17
      $R^1$ represents a $C_6$-$C_{20}$ heterocyclic or carbocyclic aryl radical, said heterocyclic radical optionally containing nitrogen or sulfur as heteroelements,
      $R^2$ represents $R^1$ or a $C_1$-$C_{30}$ linear or branched alkyl or alkenyl radical, said radicals $R^1$ and $R^2$ being optionally substituted by a $C_1$-$C_{25}$ alkoxy, $C_1$-$C_{25}$ alkyl, nitro, chloro, bromo, cyano, carboxyl, ester or mercapto group,
      m and n are integers, with n+m=v+1, v being the valence of the element A,
      (2) oxoisothiochromanium salts; and
      (3) organometallic salts of the following formula:

$(L_1L_2L_3M)^{+q}$ (VIII)

in which:
      M represents a metal from group 4 to 10,
      L1 represents 1 ligand bonded to the metal M by π electrons, the ligand being selected from the group consisting of $\eta^3$-alkyl, $\eta^5$-cyclopentadienyl and $\eta^7$-cycloheptatrienyl ligands and $\eta^6$-aromatic compounds selected from optionally substituted $\eta^6$-benzene ligands or compounds having 2 to 4 fused rings, each ring being capable of contributing to the valence layer of the metal M via 3 to 8 πelectrons, L2 represents a ligand bonded to the metal M by π electrons, the ligand being selected from the group consisting of $\eta^7$-cycloheptatrienyl ligands and $\eta^6$-aromatic compounds selected from optionally substituted $\eta^6$-benzene ligands or compounds having 2 to 4 fused rings, each ring being capable of contributing to the valence layer of the metal M via 6 or 7 π electrons, L3 represents 0 to 3 identical or different ligands bonded to the metal M by σ electrons, the ligand(s) being selected from CO and $NO_2^+$, the total electronic charge q of the complex to which L1, L2 and L3 contribute, and the ionic charge of the metal M, being positive and being 1 or 2; and b) anionic borates of the formula:

$$[BX_aR_b]^- \quad (I)$$

in which:
a and b are integers ranging from 0 to 3 for a and from 1 to 4 for b, with a+b=4,
X represents:
a halogen atom, with a=0 to 3, or
an OH function, with a=0 to 2,
the symbols R are identical or different and represent:
a phenyl radical substituted by at least one electron-withdrawing group and/or by at least two halogen atoms, when the cationic entity is an onium of an element from groups 15 to 17,
a phenyl radical substituted by at least one electron-withdrawing element or group, when the cationic entity is an organometallic complex of an element from groups 4 to 10, or
an aryl radical containing at least two aromatic nuclei, optionally substituted by at least one electron-withdrawing element or group, irrespective of the cationic entity.

5. The dental composition according to claim 1, wherein the cationic photoinitiator (D) is an iodonium salt.

6. The dental composition according to claim 1, wherein the cationic photoinitiator (D) is selected from the group consisting of the following compounds:
(P-16): $[(C_8H_{17})-O-C_6H_4-I-C_6H_5)]^+$, $[B(C_6F_5)_4]^{31}$;
(P-17): $[C_{12}H_{25}-C_6H_4-I-C_6H_5]^+$, $[B(C_6F_5)_4]^{31}$;
(P-18): $[(C_8H_{17}-O-C_6H_4)_2I]^+$, $[B(C_6F_5)_4]^-$;
(P-19): $[(C_8H_{17})-O-C_6H_4-I-C_6H_5)]^+$, $[B(C_6F_5)_4]^-$;
(P-20): $[(C_6H_5)_2S-C_6H_4-O-C_8H_{17}]^+$, $[B(C_6H_4CF_3)_4]^-$;
(P-21): $[(C_{12}H_{25}-C_6H_4)_2I]^+$, $[B(C_6F_5)_4]^-$;
(P-22): $[CH_3-C_6H_4-I-C_6H_4-CH(CH_3)_2]^+$, $[B(C_6F_5)_4]^-$;
(P-23): (η5-cyclopentadienyl)(η6-toluene)Fe$^+$, $[B(C_6F_5)_4]^-$;
(P-24): (η5-cyclopentadienyl)(η6-1-methyl-naphthalene)Fe$^+$, $[B(C_6F_5)_4]^-$;
(P-25): (η5-cyclopentadienyl)(η6-cumene)Fe$^+$, $[B(C_6F_5)_4]^-$;
(P-26): $[C_{12}H_{25}-C_6H_4)_2I]^+$, $[B(C_6H_3(CF_3)_2]^-$;
(P-27): $[CH_3-C_6H_4-I-C_6H_4-CH_2CH(CH_3)_2]^+$, $[B(C_6F_5)_4]^-$;
(P-28): $[CH_3-C_6H_4-I-C_6H_4-CH_2CH(CH_3)_2]^+$, $[B(C_6H_3(CF_3)_{-2})_4]^-$; and
(P-29): $[CH_3-C_6H_4-I-C_6H_4-CH(CH_3)_2]^+$, $[B(C_6H_3(CF_3)_2)_4]^-$.

7. The dental composition according to claim 1, wherein the cationically reactive compound (A) is selected from the group of monomers and (co)polymers consisting of:
epoxides, vinyl ethers, oxetanes, spiro-ortho-carbonates, spiro-ortho-esters and combinations thereof.

8. The dental composition according to claim 7, wherein the cationically reactive compound (A) is composed of at least one silicone oligomer or polymer (A-1) which is crosslinkable and/or polymerizable, is liquid at ambient temperature or thermofusible at a temperature lower than 100° C., and comprises:
a) at least one unit of the following formula:

(M-1)

in which:
a =0, 1 or 2,
$R^0$, identical or different at each occurrence, represents an alkyl, cycloalkyl, aryl, vinyl, hydrogeno or alkoxy radical,
Z, identical or different at each occurrence, is an organic substituent containing at least one reactive oxirane, alkenyl ether, oxetane, dioxolane and/or carbonate function, and
b) at least two silicon atoms.

9. The dental composition according to claim 8, wherein the unit (M-1) comprises groups Z selected from the group consisting of the following radicals:

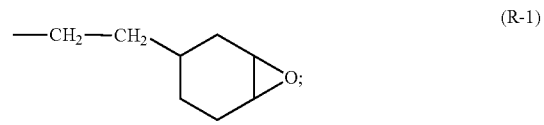
(R-1)

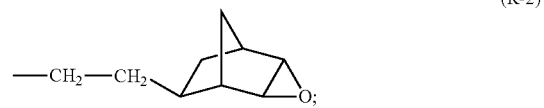
(R-2)

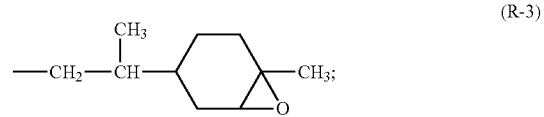
(R-3)

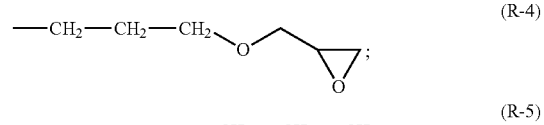
(R-4)

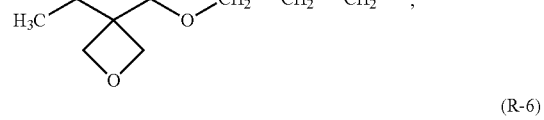
(R-5)

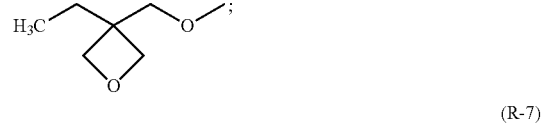
(R-6)

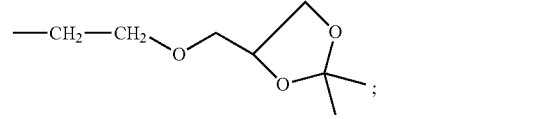
(R-7)

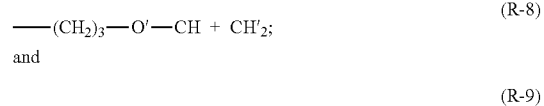
(R-8)

and

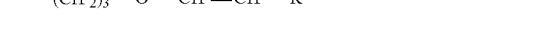
(R-9)

with R" representing a $C_1$-$C_6$ linear or branched alkyl radical.

10. The dental composition according to claim 8, wherein the cationically reactive compound (A) is a silane (G-3) of formula:

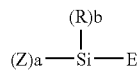

in which:

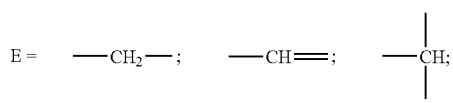

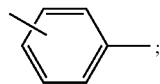

R, identical or different at each occurrence, represents an alkyl, cycloalkyl, aryl, vinyl, hydrogeno or alkoxy radical, Z, identical or different at each occurrence, is an organic substituent containing at least one oxirane, alkenyl ether, oxetane and/or carbonate function, and a+b =3.

11. The dental composition according to claim 8, wherein the cationically reactive compound (A) is a silane is selected from the group consisting of the following molecules:

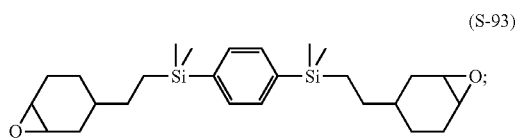
(S-93)

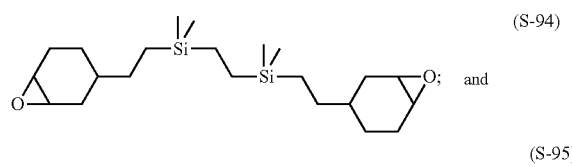
(S-94) and

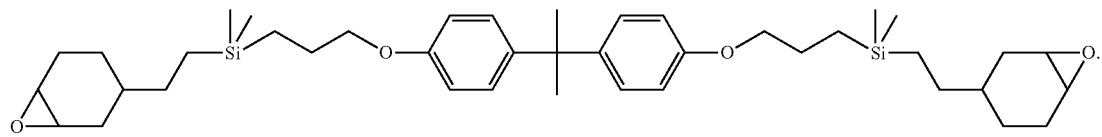
(S-95)

12. The dental composition according to claim 1, wherein the cationically reactive compound (A) is an organic compound (G-4) selected from the group consisting of the following molecules:

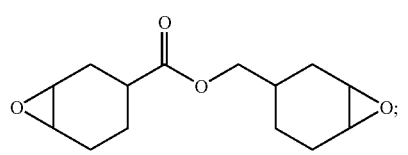
(S-96)

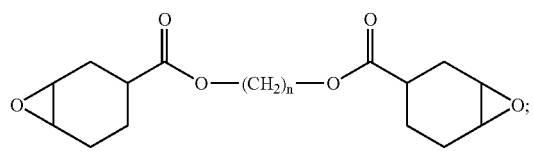
(S-97)

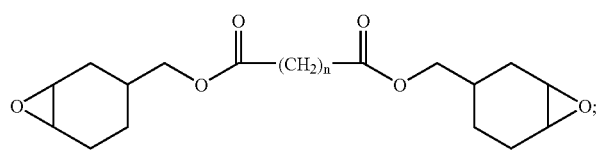
(S-98)

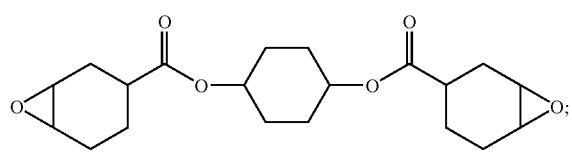
(S-99)

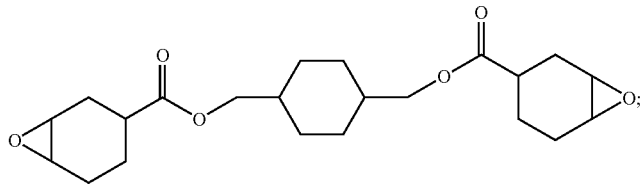
(S-100)

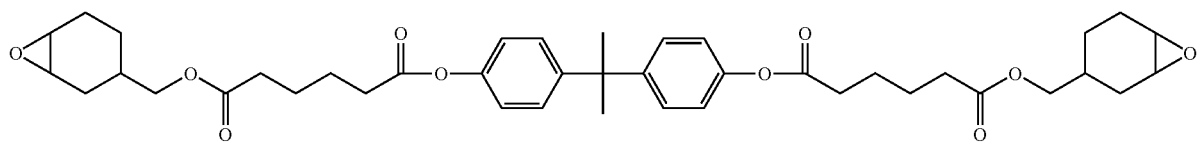
(S-101)

in which formulae n is an integer between 1 and 10 (inclusive);

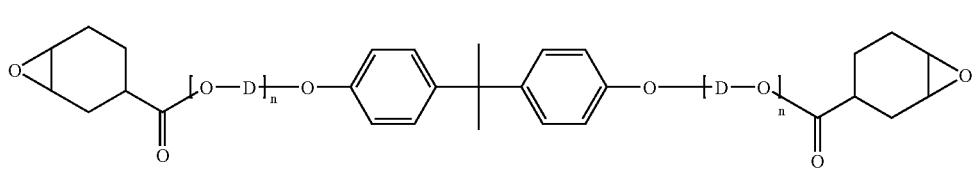
(S-103)

with n <100 and D=linear or branched $C_1$-$C_{12}$ alkyl; and

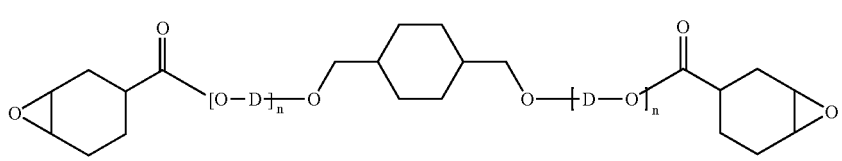
(S-104)

with n <100 and the group D =linear or branched $C_1$-$C_{12}$ alkyl.

13. A dental prosthesis obtained by polymerizing and/or crosslinking a composition according to claim 1.

14. A dental restoration material obtained by polymerizing and/or crosslinking a composition according to claim 1.

15. A compound of the formula:

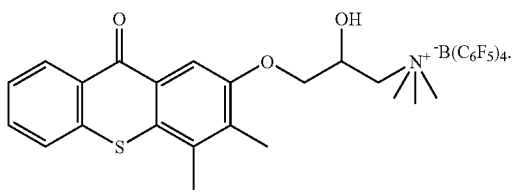
(V)

16. A compound of the formula:

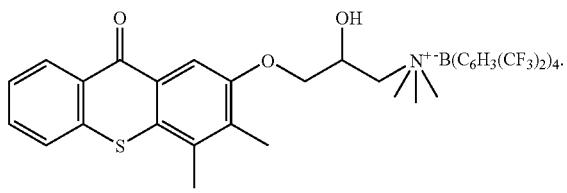
(VI)

17. A dental composition according to claim 1, wherein $R^{22}$ and $R^{23}$ are methyl, and $Y^-$ is selected from borates of the formulae $[B(C_6H_3(CF_3)_2)_4]^-$ or $[B(C_6F_5)_4]^-$.

18. A dental composition according to claim 1, wherein said electron-withdrawing group is selected from the group consisting of $CF_3$, $OCF_3$, $NO_2$ and CN.

19. A method of making a dental prosthesis or dental restoration, the method comprising exposing the dental composition of claim 1 to radiation of a wavelength greater than 390 nm.

* * * * *